(12) United States Patent
Benson et al.

(10) Patent No.: US 7,675,058 B2
(45) Date of Patent: Mar. 9, 2010

(54) N-SULFONYLAMINOCARBONYL CONTAINING COMPOUNDS

(75) Inventors: Karl E. Benson, St. Paul, MN (US);
Moses M. David, Woodbury, MN (US);
Cary A. Kipke, Woodbury, MN (US);
Brinda B. Lakshmi, Woodbury, MN (US); Charles M. Leir, Falcon Heights, MN (US); George G. Moore, Afton, MN (US); Rahul Shah, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 568 days.

(21) Appl. No.: 11/553,822

(22) Filed: Oct. 27, 2006

(65) Prior Publication Data

US 2007/0045622 A1 Mar. 1, 2007

Related U.S. Application Data

(62) Division of application No. 10/713,174, filed on Nov. 14, 2003, now Pat. No. 7,169,933.

(51) Int. Cl.
*H01L 29/08* (2006.01)
*C07D 275/04* (2006.01)

(52) U.S. Cl. .................. 257/40; 548/207; 548/209; 564/4

(58) Field of Classification Search ............ None
See application file for complete search history.

(56) References Cited

U.S. PATENT DOCUMENTS

| | | | |
|---|---|---|---|
| 2,995,542 A | 8/1961 | Brown | |
| 3,637,845 A | 2/1972 | Moore et al. | |
| 4,195,023 A | 3/1980 | Mulvey et al. | |
| 4,233,029 A | 11/1980 | Columbus et al. | |
| 4,713,389 A | 12/1987 | Salzburg et al. | |
| 4,738,708 A | 4/1988 | Borrod et al. | |
| 5,246,846 A | 9/1993 | Pittner et al. | |
| 5,674,742 A | 10/1997 | Northrup et al. | |
| 5,747,244 A | 5/1998 | Sheridan et al. | |
| 5,880,552 A | 3/1999 | McGill et al. | |
| 5,888,594 A | 3/1999 | David et al. | |
| 5,948,166 A | 9/1999 | David et al. | |
| 6,156,270 A | 12/2000 | Buechler et al. | |
| 6,369,893 B1 | 4/2002 | Christel et al. | |
| 6,656,428 B1 | 12/2003 | Clark et al. | |
| 7,078,172 B1 | 7/2006 | Okamura et al. | |
| 7,078,517 B2 | 7/2006 | Takahashi et al. | |
| 2003/0170474 A1 | 9/2003 | Qiao et al. | |
| 2003/0170881 A1 | 9/2003 | Davis et al. | |
| 2004/0082067 A1 | 4/2004 | Pozsgay | |
| 2005/0106709 A1 | 5/2005 | Benson et al. | |
| 2005/0112672 A1 | 5/2005 | Benson et al. | |
| 2005/0227076 A1 | 10/2005 | Benson et al. | |
| 2007/0015937 A1 | 1/2007 | Hintzer et al. | |

FOREIGN PATENT DOCUMENTS

| | | |
|---|---|---|
| DE | 2449365 | 4/1976 |
| EP | 0 446 047 | 9/1991 |
| EP | 0 657 737 | 6/1995 |
| WO | WO 01/11370 | 2/2001 |
| WO | WO 01/66820 A1 | 9/2001 |
| WO | WO 02/088296 | 11/2002 |
| WO | WO 03/084982 A2 | 10/2003 |
| WO | WO 03/093785 A2 | 11/2003 |

OTHER PUBLICATIONS

J.C. Martin et al. In Journal of Organic Chemistry, "Ketenes, X, Heterocyclic Systems Derived from Dimethylmalonyl Chloride", 31 pp. 2966-2972 (1966).

J. Motoyoshiya et al. In Journal of Organic Chemistry, "Peroxyoxalate Chemiluminescence of N,N-Bistosyl-1H . . . ", 67 pp. 7314-7318 (2002).

Bozhinov, et al., "Synthesis of new flame retardable sulfonamides in phase-transfer catalysis conditions", *Chemical Abstracts*, (1992), 117:235734.

Chiyomaru, et al., "2-Substituted 1,2-benzoisothiazolin-3-one 1,1-dioxides", *Chemical Abstracts*, (1972), 77:164667 XP-002331204.

Chiyomaru, et al., "Fungicides for agricultural use", *Chemical Abstracts*, (1973), 78 :144282 XP-002331203.

Chiyomaru, et al., "2-Substitued 1,2-benzoisothiazolin-3-one 1-dioxide", *Chemical Abstracts*, (1975), 82:140119.

David, M., et al., "Plasma Deposition and Etching of Diamond-Like Carbon Films", *AIChE Journal*, (Mar. 1991), vol. 37 (3), pp. 367-376.

Grate, et al., "Acoustic Wave Sensors", (1996), vol. 2, pp. 38-83, (XP002334970).

Hashimoto, et al., "Preparation of N-(phenylsulfenyl)-2-chloroacetamides as herbicides", *Chemical Abstracts*, (1991), 115:207678.

(Continued)

*Primary Examiner*—Kamal A Saeed
(74) *Attorney, Agent, or Firm*—Jean A. Lown

(57) ABSTRACT

Compounds having two reactive functional groups are described that can be used to provide a connector group between a substrate and an amine-containing material. The first reactive functional group can be used to provide attachment to a surface of a substrate. The second reactive functional group is a N-sulfonylaminocarbonyl group that can be reacted with an amine-containing material, particularly a primary aliphatic amine, to form a carbonylimino-containing connector group. The invention also provides articles and methods for immobilizing amine-containing materials to a substrate.

8 Claims, 4 Drawing Sheets

OTHER PUBLICATIONS

Iwakura, et al., "Benzenesulfonamide derivatives", *Chemical Abstracts*, (1980), 92:41570.

Kato, et al., "Syntheses of imide derivatives", *Chemical Abstracts*, (1973), 78:124224.

Kato, et al., "Electrophotographic material for lithographic plate preparation", *Chemical Abstracts*, (1994), 120:65816.

Kharasch, et al., "Reactions of atoms and free radicals in solution", *Chemical Abstracts*, (1953), 47:1656c-i.

Lahiri, et al., "Patterning Ligands on Reactive SAMs by Microcontact Printing", *Langmuir*, (1999), vol. 15, pp. 2055-2060.

Luheshi, et al., "Heterocycles by Intramolecular Aza-Wittig Reactions of Iminophosphoranes Obtained from 2-Azidobenzoyl- and 2-Azidobenzylidene Derivatives", *Tetrahedron Letters*, (1990), vol. 31, No. 45, pp. 6561-6564.

Lukovits, "Decomposition of the Wiener Topological Index. Application to Drug-Receptor Interactions", *J. Chem. Soc. Perkin Trans. II*, (1988), pp. 1667-1671.

Mandel'baum, et al., "Synthesis of derivatives of S-[1-(N-methyl-N-methylsulfonyl)carbamoylethyl]thio-and -dithiophosphoric acid", *Chemical Abstracts*, (1975), 82:57814.

Mime, et al., "2-Carbamoyl-1, 2-benzisothiazolin-3-one 1,1-dioxides", *Chemical Abstracts*, (1972), 76:14533.

Naumov, et al., "Spectra-structure correlations in solid metal saccharinates", *Chemical Abstracts*, (2002), 137:83888.

Niculescu, et al., "Redox Hydrogel-Based Amperometric Bienzyme Electrodes for Fish Freshness Monitoring", *Anal. Chem.*, (2000), vol. 72, pp. 1591-1597.

Schrader, "Esters of mono- or dithiophosphoric, phosphonic, and phosphinic acids", *Chemical Abstracts*, (1964), 60:3301.

Shah, R.R., et al., "Using Liquid Crystals to Image Reactants and Products of Acid-Base Reactions on Surfaces with Micrometer Resolution", *J. Am. Chem. Soc.*, (1999), vol. 121, pp. 11300-11310.

Shah, R.R., et al., "Principles for Measurement of Chemical Exposure Based on Recognition-Driven Anchoring Transitions in Liquid Crystals", *Science*, (2001), vol. 293, 1296.

Wagner, P., et al., "Covalent Immobilization of Native Biomolecules onto Au(111) via N-Hydroxysuccinimide Ester Functionalized Self-Assembled Monolayers for Scanning Probe Microscopy", *Biophysical. Journal*, (1996), vol. 70, pp. 2052-2066.

Wang, J., et al. "Ultrathin Porous Carbon Films as Amperometric Transducers for Biocatalytic Sensors", *Anal. Chem.*, (1994), vol. 66, pp. 1988-1992.

Webb, et al., "Appraisal of ethylene production as a test for defoliants", *Chemical Abstracts*, (1975), 83:189238.

Yamahara, et al., "Radiation sensitive resin composition", *Chemical Abstracts*, (2000), 133:357243.

N-SULFONYLAMINOCARBONYL CONTAINING COMPOUNDS

CROSS REFERENCE TO RELATED APPLICATIONS

This application is a divisional of U.S. Ser. No. 10/713,174, filed on Nov. 14, 2003, now U.S. Pat No. 7,169,933, the disclosure of which is herein incorporated by reference.

FIELD OF THE INVENTION

This invention provides compounds that include both a substrate-reactive group and a N-sulfonylaminocarbonyl group. The invention also provides articles and methods for immobilizing amine-containing materials to a substrate.

BACKGROUND

Amine-containing materials such as amine-containing analytes, amino acids, DNA fragments, RNA fragments, protein fragments, organelles, and immunoglobins immobilized on the surface of a substrate can be used in numerous applications. For example, immobilized biological amines can be used for the medical diagnosis of a disease or genetic defect, for biological separations, or for detection of various biomolecules.

The attachment of amine-containing materials to a substrate is often achieved through the use of a tethering compound. A tethering compound usually has two reactive functional groups separated by a linking group. One of the functional groups provides a means for anchoring the tethering compound to a substrate by reacting with a complementary functional group on the surface of the substrate. A second reactive functional group can be selected to react with an amine-containing material. The second reactive functional group can be, for example, an activated acyl derivative, such as an N-hydroxysuccinimide ester, or a cyclic azlactone. An amine-containing material can react with the N-hydroxysuccinimide ester to form a carboxamide resulting in the displacement of an N-hydroxysuccinimide fragment. An amine-containing material can react with the cyclic azlactone resulting in an opening of the ring structure.

Although tethering compounds that include a group such as an N-hydroxysuccinimide ester or a cyclic azlactone can be highly reactive with primary amine-containing materials, such tethering compounds can suffer from a number of disadvantages. Many of the reactions with biological amines are conducted in dilute aqueous solutions. Under these conditions, the N-hydroxysuccinimide ester functional group is known to undergo rapid hydrolysis. This competing reaction can cause incomplete or inefficient immobilization of the amine-containing materials on the substrate. While cyclic azlactone functional groups are more stable to hydrolysis, cyclic azlactone groups tend to be synthetically incompatible with many groups that could be used to attach the tethering compound to a substrate.

SUMMARY

Compounds are provided that can function as tethering compounds for immobilizing an amine-containing material to a substrate. The compounds include two types of reactive functional groups. The first type of reactive functional group is a substrate-reactive group capable of reacting with a complementary functional group on the surface of a substrate resulting in the attachment of a tethering group to the substrate. The second type of reactive functional group is a N-sulfonylaminocarbonyl derivative that can react with an amine-containing material by a nucleophilic displacement reaction. A connector group is formed between the substrate and the amine-containing material. Articles and methods for immobilizing amine-containing materials to a substrate are also provided.

One aspect of the invention provides compounds that can be attached to a substrate and that can react with an amine-containing material. The compounds are of Formula I:

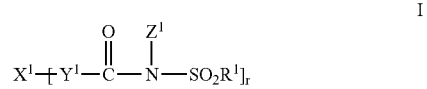

wherein $X^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group;

$Y^1$ is a single bond or a divalent group selected from an alkylene, heteroalkylene, arylene, carbonyl, carbonyloxy, carbonylimino, oxy, thio, —$NR^d$— where $R^d$ is hydrogen or alkyl, or combinations thereof;

$Z^1$ is an alkyl, aryl, or —(CO)$R^a$ wherein $R^a$ together with $R^1$ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

$R^1$ is an alkyl, fluoroalkyl, chloroalkyl, aryl, —$NR^bR^c$ wherein $R^b$ and $R^c$ are each an alkyl group or taken together with the nitrogen atom to which they are attached form a four to eight membered cyclic group, or $R^1$ taken together with $R^a$ and the groups to which they are attached form the four to eight membered heterocyclic or heterobicyclic group that can be fused to the optional aromatic group, optional saturated or unsaturated cyclic group, or optional saturated or unsaturated bicyclic group; and r is equal to 1 when $X^1$ is a monovalent group or equal to 2 when $X^1$ is a divalent group. The compound of Formula I can be unsubstituted or substituted with a halo, alkyl, alkoxy, or combinations thereof.

Another aspect of the invention provides articles that include a tethering group attached to a substrate. The tethering group is the reaction product of the substrate-reactive group $X^1$ in compounds of Formula I with a complementary functional group on the surface of the substrate to form an ionic bond, covalent bond, or a combination thereof. The substrate-attached tethering group has a N-sulfonylaminocarbonyl group capable of reacting with an amine-containing material.

Yet another aspect of the invention provides a method of immobilizing an amine-containing material to a substrate. The method involves preparing a substrate-attached tethering group by reacting the substrate-reactive group $X^1$ in compounds of Formula I with a complementary functional group on a substrate; and reacting a N-sulfonylaminocarbonyl group of the substrate-attached tethering group with an amine-containing material to form a connector group between the substrate and the amine-containing material.

The invention also provides a multilayer substrate that includes a polymeric layer, a layer of diamond-like glass, and a layer of diamond-like carbon positioned between the polymeric layer and the diamond-like glass layer. A tethering group that includes a N-sulfonylaminocarbonyl group can be attached to the diamond-like glass layer of the multilayer substrate.

The above summary of the present invention is not intended to describe each disclosed embodiment or every implementation of the present invention. The Figures and the detailed description that follow more particularly exemplify these embodiments.

BRIEF DESCRIPTION OF THE DRAWINGS

The above aspects may be more completely understood in consideration of the following detailed description of various embodiments in connection with the accompanying drawings, in which.

Figure 1:
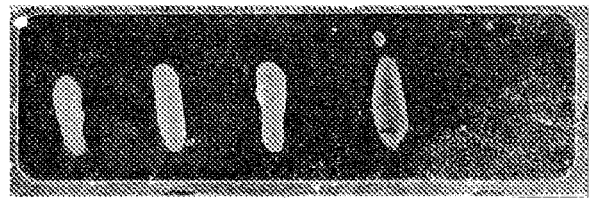
FIG. 1 is a confocal micrograph of various concentrations (50 micrograms/ml, 25 micrograms/ml, 12.5 micrograms/ml, and 6.25 micrograms/ml from left to right) of fluorescence labeled mouse IgG immobilized by reacting with N-sulfonylaminocarbonyl tethering groups attached to a substrate.

While the invention is amenable to various modifications and alternative forms, specifics thereof have been shown by way of example in the drawings and will be described in detail. It should be understood, however, that the intention is not to limit the invention to the particular embodiments described. To the contrary, the intention is to cover all modifications, equivalents, and alternatives falling within the spirit and scope of the present disclosure.

DETAILED DESCRIPTION

Compounds having two reactive functional groups are described that can be used to provide a connector group between a substrate and an amine-containing material. The first reactive functional group can be used to provide attachment of a tethering group to a surface of a substrate. The second reactive functional group is a N-sulfonylaminocarbonyl group that can be reacted with an amine-containing material, particularly a primary aliphatic amine-containing material, to form a carbonylimino-containing connector group. The invention also provides articles and methods for immobilizing amine-containing materials to a substrate.

Definitions

As used herein, the terms "a", "an", and "the" are used interchangeably with "at least one" to mean one or more of the elements being described.

As used herein, the term "acyl" refers to a monovalent group of formula —(CO)R where R is an alkyl group and where (CO) used herein indicates that the carbon is attached to the oxygen with a double bond.

As used herein, the term "acyloxy" refers to a monovalent group of formula —O(CO)R where R is an alkyl group.

As used herein, the term "acyloxysilyl" refers to a monovalent group having an acyloxy group attached to a Si (i.e., Si—O(CO)R where R is an alkyl). For example, an acyloxysilyl can have a formula —Si[O(CO)R]$_{3-n}$L$_n$ where n is an integer of 0 to 2 and L is a halogen or alkoxy. Specific examples include —Si[O(CO)CH$_3$]$_3$, —Si[O(CO)CH$_3$]$_2$Cl, or —Si[O(CO)CH$_3$]Cl$_2$.

As used herein, the term "alkoxy" refers to a monovalent group of formula —OR where R is an alkyl group.

As used herein, the term "alkoxycarbonyl" refers to a monovalent group of formula —(CO)OR where R is an alkyl group.

As used herein, the term "alkoxysilyl" refers to a group having an alkoxy group attached to a Si (i.e., Si—OR where R is an alkyl). For example, an alkoxysilyl can have a formula —Si(OR)$_{3-n}$(L$^a$)$_n$ where n is an integer of 0 to 2 and L$^a$ is a halogen or acyloxy. Specific examples include —Si(OCH$_3$)$_3$, —Si(OCH$_3$)$_2$Cl, or —Si(OCH$_3$)Cl$_2$.

As used herein, the term "alkyl" refers to a monovalent radical of an alkane and includes groups that are linear, branched, cyclic, or combinations thereof. The alkyl group typically has 1 to 30 carbon atoms. In some embodiments, the alkyl group contains 1 to 20 carbon atoms, 1 to 10 carbon atoms, 1 to 6 carbon atoms, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

As used herein, the term "alkyl disulfide" refers to a monovalent group of formula —SSR where R is an alkyl group.

As used herein, the term "alkylene" refers to a divalent radical of an alkane. The alkylene can be straight-chained, branched, cyclic, or combinations thereof. The alkylene typically has 1 to 200 carbon atoms. In some embodiments, the alkylene contains 1 to 100, 1 to 80, 1 to 50, 1 to 30, 1 to 20, 1 to 10, or 1 to 4 carbon atoms. The radical centers of the alkylene can be on the same carbon atom (i.e., an alkylidene) or on different carbon atoms.

As used herein, the term "aralkyl" refers to a monovalent radical of the compound R—Ar where Ar is an aromatic carbocyclic group and R is an alkyl group.

As used herein, the term "aralkylene" refers to a divalent radical of formula —R—Ar— where Ar is an arylene group and R is an alkylene group.

As used herein, the term "aryl" refers to a monovalent aromatic carbocyclic radical. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "arylene" refers to a divalent radical of a carbocyclic aromatic compound having one to 5 rings that are connected, fused, or combinations thereof. In some embodiments, the arylene group has up to 5 rings, up to 4 rings, up to 3 rings, up to 2 rings, or one aromatic ring. For example, the arylene group can be phenylene.

As used herein, the term "azido" refers to a group of formula —N₃.

As used herein, the term "aziridinyl" refers to a cyclic monovalent radical of aziridine having the formula

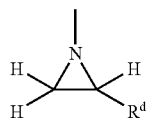

where $R^d$ is hydrogen or alkyl.

As used herein, the term "benzotriazolyl" refers to a monovalent group having a benzene group fused to a triazolyl group. The formula for a benzotriazolyl group is $C_6H_4N_3$—.

As used herein, the term "carbonyl" refers to a divalent group of formula —(CO)—.

As used herein, the term "carbonylimino" refers to a divalent group of formula —(CO)NR⁴— where R⁴ is hydrogen, alkyl, or aryl.

As used herein, the term "carbonyloxy" refers to a divalent group of formula —(CO)O—.

As used herein, the term "carbonyloxycarbonyl" refers to a divalent group of formula —(CO)O(CO)—. Such a group is part of an anhydride compound.

As used herein, the term "carbonylthio" refers to a divalent group of formula —(CO)S—.

As used herein, the term "carboxy" refers to a monovalent group of formula —(CO)OH.

As used herein, the term "chloroalkyl" refers to an alkyl having at least one hydrogen atom replaced with a chlorine atom.

As used herein, the term "cyano" refers to a group of formula —CN.

As used herein, the term "disulfide" refers to a divalent group of formula —S—S—.

As used herein, the term "ethylenically unsaturated" refers to a monovalent group having a carbon-carbon double bond of formula —CY═CH₂ where Y is hydrogen, alkyl, or aryl.

As used herein, the term "fluoroalkyl" refers to an alkyl having at least one hydrogen atom replaced with a fluorine atom.

As used herein, the term "haloalkyl" refers to an alkyl having at least one hydrogen atom replaced with a halogen selected from F, Cl, Br, or I. Perfluoroalkyl groups are a subset of haloalkyl groups.

As used herein, the term "halocarbonyloxy" refers to a monovalent group of formula —O(CO)X where X is a halogen atom selected from F, Cl, Br, or I.

As used herein, the term "halocarbonyl" refers to a monovalent group of formula —(CO)X where X is a halogen atom selected from F, Cl, Br, or I.

As used herein, the term "halosilyl" refers to a group having a Si attached to a halogen (i.e., Si—X where X is a halogen). For example, the halosilyl group can be of formula —SiX$_{3-n}$(L$^b$)$_n$ where n is an integer of 0 to 2 and L$^b$ is selected from an alkoxy, or acyloxy. Some specific examples include the groups —SiCl₃, —SiCl₂OCH₃, and —SiCl(OCH₃)₂.

As used herein, the term "heteroalkylene" refers to a divalent alkylene having one or more carbon atoms replaced with a sulfur, oxygen, or NR$^d$ where R$^d$ is hydrogen or alkyl. The heteroalkylene can be linear, branched, cyclic, or combinations thereof and can include up to 400 carbon atoms and up to 30 heteroatoms. In some embodiments, the heteroalkylene includes up to 300 carbon atoms, up to 200 carbon atoms, up to 100 carbon atoms, up to 50 carbon atoms, up to 30 carbon atoms, up to 20 carbon atoms, or up to 10 carbon atoms.

As used herein, the term "hydroxy" refers to a group of formula —OH.

As used herein, the term "isocyanato" refers to a group of formula —NCO.

As used herein, the term "mercapto" refers to a group of formula —SH.

As used herein, the term "N-sulfonylaminocarbonyl" refers to a divalent entity of formula —SO₂NZ$^a$(CO)— where Z$^a$ is an alkyl, aryl, or part of a group structure.

As used herein, the term "oxy" refers to a divalent group of formula —O—.

As used herein, the term "oxycarbonylimino" refers to a divalent group of formula —O(CO)NR⁴— where R⁴ is hydrogen, alkyl, or aryl.

As used herein, the term "oxycarbonyloxy" refers to a divalent group of formula —O(CO)O—.

As used herein, the term "oxycarbonylthio" refers to a divalent group of formula —O(CO)S—.

As used herein, the term "perfluoroalkyl" refers to an alkyl group in which all of the hydrogen atoms are replaced with fluorine atoms. Perfluoroalkyl groups are a subset of fluoroalkyl groups.

As used herein, the term "phosphato" refers to a monovalent group of formula —OPO₃H₂.

As used herein, the term "phosphono" refers to a monovalent group of formula —PO₃H₂.

As used herein, the term "phosphoramido" refers to a monovalent group of formula —NHPO₃H₂.

As used herein, the term "primary aromatic amino" refers to a monovalent group of formula —ArNH₂ where Ar is an aryl group.

As used herein, the term "secondary aromatic amino" refers to a monovalent group of formula —ArNR$^h$H where Ar is an aryl group and R$^h$ is an alkyl or aryl.

As used herein, the term "tertiary amino" refers to a group of formula —NR₂ where R is an alkyl.

As used herein, the term "thio" refers to a divalent group of formula —S—.

As used herein, the term "thiocarbonylimino" refers to a divalent group of formula —S(CO)NR⁴— where R⁴ is hydrogen, alkyl, or aryl.

As used herein, the term "attachment group" refers to the group formed by reaction of a substrate-reactive group in a compound according to Formula I with a complementary functional group on the surface of a substrate.

As used herein, the term "complementary functional group" refers to a group capable of reacting with a recited group to form an ionic bond, covalent bond, or combinations thereof. For example, the complementary functional group can be a group on a substrate capable of reacting with group X¹ in Formula I.

As used herein, the term "connector group" refers to a group linking a substrate to an immobilized amine-containing material. The attachment group is part of the connector group.

As used herein, the term "room temperature" refers to a temperature of about 20° C. to about 25° C. or about 22° C. to about 25° C.

As used herein, the term "substrate" refers to a solid phase support to which the tethering compounds of the invention can be attached. The substrates can have any useful form including, but not limited to, thin films, sheets, membranes, filters, nonwoven or woven fibers, hollow or solid beads, bottles, plates, tubes, rods, pipes, or wafers. The substrates can be porous or non-porous, rigid or flexible, transparent or opaque, clear or colored, or reflective or non-reflective. Suitable substrate materials include, for example, polymeric materials, glasses, ceramics, metals, metal oxides, hydrated metal oxides, or combinations thereof.

As used herein, the term "tethering compound" refers to a compound that has two reactive groups. One of the reactive groups (i.e., the substrate-reactive functional group) can react with a complementary functional group on the surface of a substrate to form a tethering group. The other reactive group (i.e., the N-sulfonylaminocarbonyl group) can react with an amine-containing material. Reaction of both reactive groups of the tethering compound results in the formation of a connector group between the substrate and the amine-containing material (i.e., the amine-containing material can be immobilized on the substrate).

As used herein, the term "tethering group" refers to a group attached to a substrate that results from the reaction of a tethering compound with a complementary functional group on the surface of the substrate with a tethering compound. The tethering group includes a group that can react with an amine-containing material. The tethering group includes a N-sulfonylaminocarbonyl group. The attachment group is part of the tethering group.

As used herein, a curve connecting two groups in a formula indicates that the two groups together form part of a cyclic structure.

Compounds

One aspect of the invention provides tethering compounds. The compounds include both a substrate-reactive group and a N-sulfonylaminocarbonyl group. The substrate-reactive group can be used for attachment to a substrate and the N-sulfonylaminocarbonyl group can be reacted with an amine-containing material to form a carbonylimino-containing connector group resulting in the immobilization of the amine-containing material to a substrate. That is, the compounds can be reacted to provide a connector group between a substrate and an amine-containing material.

The compounds are of Formula I:

I wherein $X^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group;

$Y^1$ is a single bond or a divalent group selected from an alkylene, heteroalkylene, arylene, carbonyl, carbonyloxy, carbonylimino, oxy, thio, —$NR^d$— where $R^d$ is hydrogen or alkyl, or combinations thereof;

$Z^1$ is an alkyl, aryl, or —(CO)$R^a$ wherein $R^a$ together with $R^1$ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

$R^1$ is an alkyl, fluoroalkyl, chloroalkyl, aryl, —$NR^bR^c$ wherein $R^b$ and $R^c$ are each an alkyl group or taken together with the nitrogen atom to which they are attached form a four to eight membered cyclic group, or $R^1$ together with $R^a$ and the groups to which they are attached form the four to eight membered heterocyclic or heterobicyclic group that can be fused to the optional aromatic group, optional saturated or unsaturated cyclic group, or optional saturated or unsaturated bicyclic group; and r is equal to 1 when $X^1$ is a monovalent group or equal to 2 when $X^1$ is a divalent group. The compounds of Formula I can be unsubstituted or substituted with a halo, alkyl, alkoxy, or combinations thereof.

The functional group $X^1$ typically does not react with a group —(CO)$NZ^1SO_2R^1$ in Formula I and can be used, for example, to provide attachment to a substrate by reacting with a complementary functional group on the surface of the substrate. That is, $X^1$ in compounds of Formula I can react with a complementary functional group to form a substrate-attached tethering group. $X^1$ can be monovalent or divalent. When $X^1$ is divalent, r in Formula I is equal to 2 and the compound has the following structure:

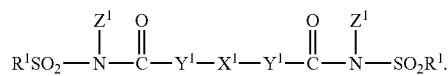

The compound can be symmetrical about $X^1$. A disulfide is an exemplary divalent $X^1$ group. When $X^1$ is monovalent, r in Formula I is equal to 1 and the compound has the following structure:

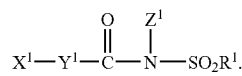

Suitable monovalent $X^1$ groups include a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group.

The $X^1$ groups typically can react with a complementary functional group on the surface of a substrate to form an ionic bond, covalent bond, or combination thereof. Suitable $X^1$ groups for attachment to the surface of a polymeric substrate include a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, or ethylenically unsaturated group. Suitable $X^1$ groups for attachment to the surface of a gold-containing substrate include mercapto, disulfide, or alkyl disulfide. Suitable $X^1$ groups for attachment to the surface of other metal-containing substrates include benzotriazolyl, phosphono, phosphoroamido, or phosphato groups. Suitable $X^1$ groups for attachment to glass or ceramic-containing substrates as well as to metal oxide-containing or hydrated metal oxide-containing substrates include halosilyl, alkoxysilyl, or acyloxysilyl groups.

The group $Y^1$ in Formula I can be a single bond or a divalent group selected from an alkylene, heteroalkylene, arylene, carbonyl, carbonyloxy, carbonylimino, oxy, thio, —$NR^d$— where $R^d$ is hydrogen or alkyl, or combinations thereof. Suitable heteroalkylenes usually contain 1 to 400 carbon atoms and up to 30 heteroatoms selected from N, O, S, or combinations thereof. Suitable alkylenes usually contain 1 to 200 carbon atoms. The heteroalkylene and alkylene groups can be linear, branched, cyclic, or combinations thereof.

The group $Y^1$, for example, can include an alkylene group as in the following formula:

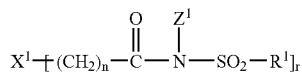

where n is an integer of 1 to 100. Exemplary compounds include those where n is an integer no greater than 80, no greater than 60, no greater than 40, no greater than 20, or no greater than 10. The groups $X^1$, r, $Z^1$, and $R^1$ are the same as previously defined for Formula I. The compounds can be unsubstituted or substituted with a halo, alkyl, alkoxy, or combinations thereof.

In some compounds according to Formula I, $Y^1$ includes a first alkylene group that is linked to a second alkylene or a first heteroalkylene group with a group selected from a carbonyl, carbonyloxy, carbonylimino, oxy, thio, or —$NR^d$— where $R^d$ is hydrogen or alkyl. Additional alkylene or heteroalkylene groups can be linked to the second alkylene or to the first heteroalkylene group with a group selected from a carbonyl, carbonyloxy, carbonylimino, oxy, thio, or —$NR^d$— where $R^d$ is hydrogen or alkyl. In other compounds according to Formula I, $Y^1$ includes a first heteroalkylene group that is linked to a second heteroalkylene or to a first alkylene group with a group selected from a carbonyl, carbonyloxy, carbonylimino oxy, thio, or —$NR^d$— where $R^d$ is hydrogen or alkyl. Additional alkylene or heteroalkylene groups can be linked to the second heteroalkylene or to the first alkylene group with a group selected from a carbonyl, carbonyloxy, carbonylimino group, oxy, thio, —$NR^d$— where $R^d$ is hydrogen or alkyl.

For example, compounds can have the following formula:

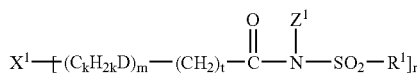

where D is oxygen, sulfur, or NH; m is an integer of 1 to 200; t is an integer of 0 to 12; and k is an integer of 2 to 4. Exemplary compounds include those where m is an integer no greater than 150, no greater than 100, no greater than 80, no greater than 60, no greater than 40, no greater than 20, or no greater than 10; t is an integer no greater than 10, no greater than 8, no greater than 6, no greater than 4, no greater than 2, or equal to 0; and k is no greater than 3, no greater than 2, or equal to 1. In some compounds, the heteroatom D is oxygen and k is equal to 2. The groups $X^1$, r, $Z^1$, and $R^1$ are the same as previously defined for Formula I. The compounds can be unsubstituted or substituted with a halo, alkyl, alkoxy, or combinations thereof.

In other examples, the group $Y^1$ can include a combination of alkylene and heteroalkylene groups that are separated by a carbonyl, carbonyloxy, carbonylimino, oxy, thio, —$NR^d$— where $R^d$ is hydrogen or alkyl, or combinations thereof:

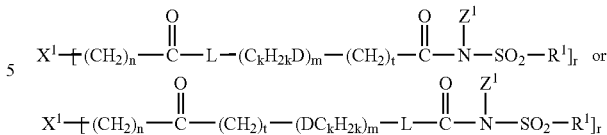

where D is oxygen, sulfur, or NH; n is an integer of 1 to 100; m is an integer of 1 to 200; t is an integer of 0 to 12; k is an integer of 2 to 4; and L is oxygen or $NR^d$ where $R^d$ is hydrogen or alkyl. The positions of the alkylene groups and the heteroalkylene groups can be reversed. Exemplary compounds include those where n is an integer no greater than 80, no greater than 60, no greater than 40, no greater than 20, or no greater than 10; m is an integer no greater than 150, no greater than 100, no greater than 80, no greater than 60, no greater than 40, no greater than 20, or no greater than 10; t is an integer no greater than 10, no greater than 8, no greater than 6, no greater than 4, no greater than 2, or equal to 0; and k is an integer no greater than 3, no greater than 2, or equal to 1. In some compounds, the D group is oxygen and k is equal to 2. The groups $X^1$, r, $Z^1$, and $R^1$ are the same as previously defined for Formula I. The compounds can be unsubstituted or substituted with a halo, alkyl, alkoxy, or combinations thereof.

In other examples, the compound can have one the following formulas:

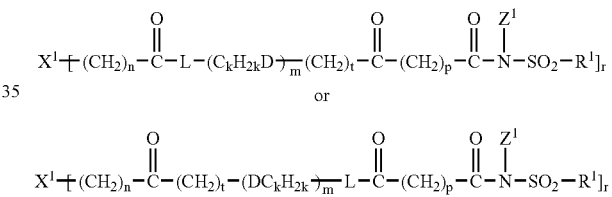

where D is oxygen, sulfur, or NH; n is an integer of 1 to 100; m is an integer of 1 to 200; p is an integer of 1 to 10; t is an integer of 0 to 12; k is an integer of 2 to 4; and L is oxygen or $NR^d$ where $R^d$ is hydrogen or alkyl. Exemplary compounds include those in which n is an integer no greater than 80, no greater than 60, no greater than 40, no greater than 20, or no greater than 10; m is an integer no greater than 150, no greater than 100, no greater than 80, no greater than 60, no greater than 40, no greater than 20, or no greater than 10; p is an integer no greater than 8, no greater than 6, no greater than 4, or no greater than 2; t is an integer no greater than 10, no greater than 8, no greater than 6, no greater than 4, no greater than 2, or equal to 0; and k is an integer no greater than 3, no greater than 2, or equal to 1. In some compounds, the heteroatom D is oxygen and k is equal to 2. The groups $X^1$, r, $Z^1$, and $R^1$ are the same as previously defined for Formula I. The compounds can be unsubstituted or substituted with a halo, alkyl, alkoxy, or combinations thereof In some embodiments, $Y^1$ can include an arylene group in addition to one or more alkylene groups and one or more heteroalkylene groups. The arylene can be bonded directly to the N-sulfonylaminocarbonyl group. The arylene group can include up to 30 carbon atoms, up to 24 carbon atoms, up to 18 carbon atoms, up to 12 carbon atoms, or 6 carbon atoms. In some embodiments, the compounds can have one of the following formulas:

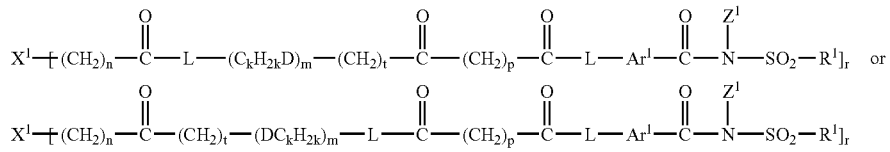

where D is oxygen, sulfur, or NH; n is an integer of 1 to 100; m is an integer of 1 to 200; p is an integer of 1 to 10; t is an integer of 0 to 12; k is an integer of 2 to 4; $Ar^1$ is an arylene group; and L is oxygen or $NR^d$ where $R^d$ is hydrogen or alkyl. Exemplary compounds include those where n is an integer no greater than 80, no greater than 60, no greater than 40, no greater than 20, or no greater than 10; m is an integer no greater than 100, no greater than 80, no greater than 60, no greater than 40, no greater than 20, or no greater than 10; p is an integer no greater than 8, no greater than 6, no greater than 4, or no greater than 2; t is an integer no greater than 10, no greater than 8, no greater than 6, no greater than 4, no greater than 2, or equal to 0; and k is an integer no greater than 3, no greater than 2, or equal to 1. In some compounds of the above formula, D is oxygen, k is equal to 2, and $Ar^1$ is phenylene as in one of the following structures:

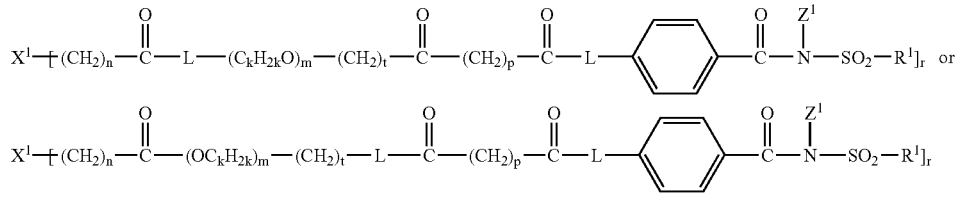

The groups $X^1$, r, $Z^1$, and $R^1$ are the same as previously defined for Formula I. The compounds can be unsubstituted or substituted with a halo, alkyl, alkoxy, or combinations thereof.

The group $Y^1$ can be an arylene group as in the following structure:

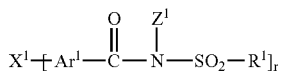

where $Ar^1$ is an arylene group. In some compounds, $Ar^1$ is phenylene. The groups $X^1$, r, $Z^1$, and $R^1$ are the same as previously defined for Formula I. The compounds can be unsubstituted or substituted with a halo, alkyl, alkoxy, or combinations thereof.

$Y^1$ can be a single bond. For example, in the following formula, Y is a single bond when $X^1$ is a primary or secondary aromatic amino group.

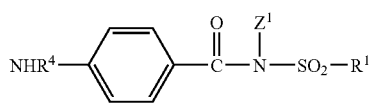

In this formula, $R^4$ is hydrogen, aryl, alkyl. The groups $Z^1$ and $R^1$ are the same as previously defined for Formula I. The compounds can be unsubstituted or substituted with a halo, alkyl, alkoxy, or combinations thereof.

The group $Z^1$ in some embodiments of Formula I can be alkyl or aryl. For example, $Z^1$ can be a $C_{1-30}$ alkyl, a $C_{1-10}$ alkyl, or a $C_{1-6}$ alkyl. In other examples, $Z^1$ can be a $C_{6-30}$ aryl, a $C_{6-24}$ aryl, a $C_{6-18}$ aryl, or a $C_{6-12}$ aryl. In other embodiments of Formula I, $Z^1$ can be a —(CO)$R^a$ group that together with $R^1$ and the groups to which they are attached form a heterocyclic or heterobicyclic group that can be fused to an optional aromatic group, optional saturated or unsaturated cyclic group, or optional saturated or unsaturated bicyclic group. The heterocyclic or heterobicyclic group includes a nitrogen and sulfur heteroatom. An exemplary heterocyclic group fused to an aromatic group is shown in the following formula:

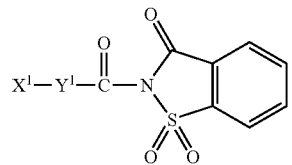

where $X^1$ is monovalent or

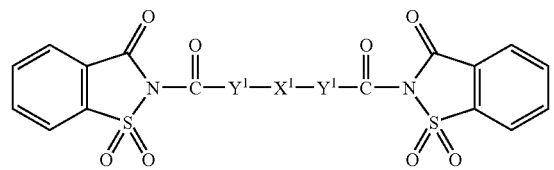

where $X^1$ is divalent.

As alternatives to combining with $Z^1$ to form a heterocyclic or heterobicyclic structure, $R^1$ can be an alkyl, fluoroalkyl, chloroalkyl, aryl, or —$NR^bR^c$ group where Rb and $R_c$ are each an alkyl or taken together with the nitrogen atom to which they are attached form a four to eight membered heterocyclic group. In some embodiments, $R^1$ can be a $C_{1-30}$ alkyl, a $C_{1-10}$ alkyl, or a $C_{1-6}$ alkyl. In other embodiments, $R^1$ can be a $C_{1-30}$ fluoroalkyl, a $C_{1-10}$ fluoroalkyl, or a $C_{14}$ perfluoroalkyl group. In still other embodiments, $R^1$ can be a $C_{6-30}$ aryl, a $C_{6-18}$ aryl, or a $C_{6-12}$ aryl. For example $R^1$ can be a phenyl group.

Exemplary compounds according to Formula I include, but are not limited to, the following:
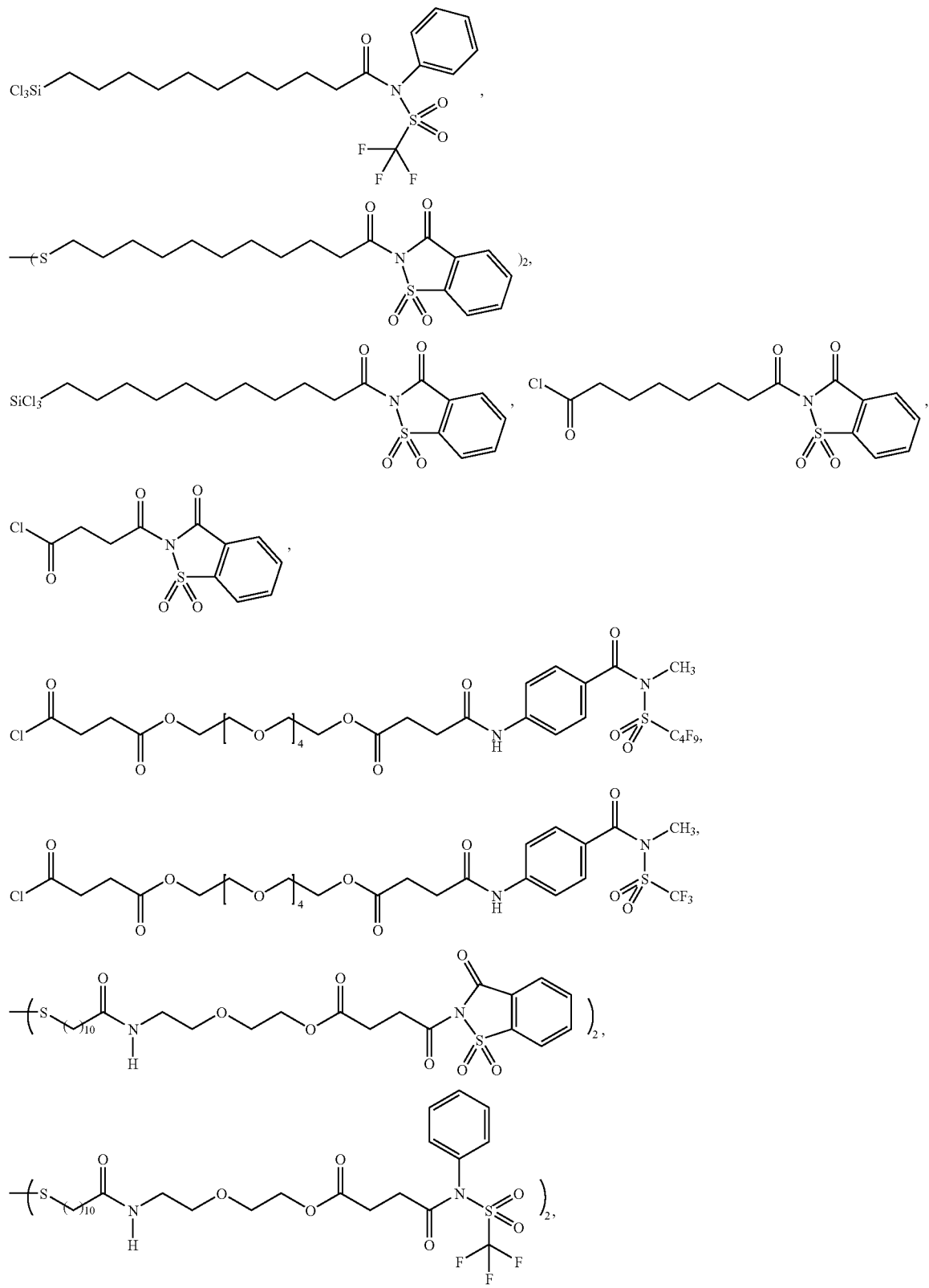

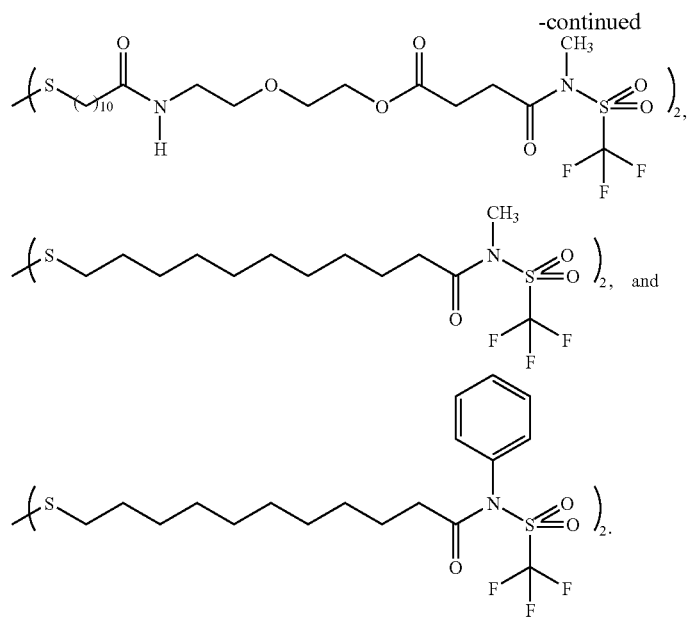

Any of these compounds or any other compound that is within the scope of Formula I can be unsubstituted or substituted with a halo, alkyl, alkoxy, or combinations thereof.

Method of Preparing Compounds

The compounds of Formulas I may be prepared, for example, by reaction of a first compound having a nitrogen-containing group with a second compound that includes a halocarbonyl group. More specifically, the nitrogen-containing group of the first compound includes a nitrogen atom directly bonded to a sulfonyl group as well as to at least one hydrogen atom. The first compound can further include a substrate-reactive group $X^1$ or a group that can be converted to a substrate-reactive group $X^1$. The substrate-reactive groups do not react, or react slowly, with the halocarbonyl group of the second compound such that the nitrogen-containing group of the first compound reacts preferentially with the halocarbonyl group of the second compound. A suitable reaction scheme is shown in Reaction Scheme A.

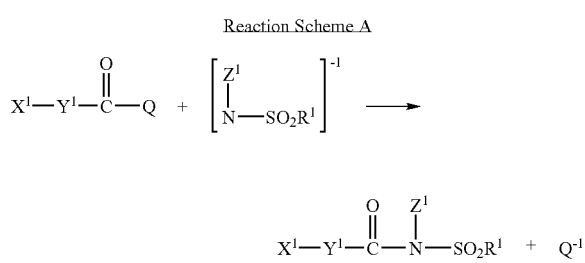

The —(CO)Q group can be a halocarbonyl group. The groups $X^1$, $Y^1$, $Z^1$, and $R^1$ can be the same as previously defined for Formula I. Where $Z^1$ in Formula I is the —(CO)$R^a$ and $R^a$ combines with $R^1$ to form a ring structure, the compounds can be prepared using reaction Scheme A'.

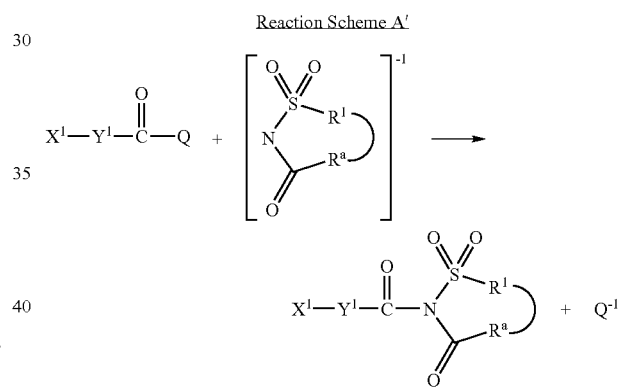

where $R^a$, $R^1$, $X^1$, and $Y^1$ are as previously defined for Formula I. The —(CO)Q group can be a halocarbonyl group.

Articles

Another aspect of the invention provides articles that include a tethering group attached to a substrate (i.e., a substrate-attached tethering group). The substrate-attached tethering group is the reaction product of a complementary functional group G on a surface of a substrate with the group $X^1$ in compounds of Formula I. The substrate-attached tethering group has a N-sulfonylaminocarbonyl group that can react with an amine-containing material to form a carbonylimino-containing connector group between a substrate and an amine-containing material.

The substrate is a solid phase material to which the tethering groups can be attached. The substrate is not soluble in a solution used to attach a compound of Formula I to the surface of the substrate. Typically, a tethering group is attached only to an outer portion of the substrate and a bulk portion of the substrate is not modified during the process of attaching tethering group to the substrate. If the substrate has groups G distributed throughout the substrate, only those groups in the outer portion (e.g., on or near the surface) are usually capable of reacting with group $X^1$ of the compounds according to Formula I.

The substrates can have any useful form including, but not limited to, thin films, sheets, membranes, filters, nonwoven or woven fibers, hollow or solid beads, bottles, plates, tubes, rods, pipes, or wafers. The substrates can be porous or nonporous, rigid or flexible, transparent or opaque, clear or colored, and reflective or non-reflective. Suitable substrate materials include, for example, polymeric materials, glasses, ceramics, metals, metal oxides, hydrated metal oxides, or combinations thereof.

The substrates can have a single layer or multiple layers of material. For example, the substrate can have one or more second layers that provide support for a first layer that includes a complementary functional group capable of reacting with the $X^1$ group in compound of Formula I. The first layer is the outer layer of the substrate. In some embodiments, a surface of a second layer is chemically modified or coated with another material to provide a first layer that includes a complementary functional group capable of reacting with the $X^1$ group.

Suitable polymeric substrate materials include, but are not limited to, polyolefins, polystyrenes, polyacrylates, polymethacrylates, polyacrylonitriles, poly(vinylacetates), polyvinyl alcohols, polyvinyl chlorides, polyoxymethylenes, polycarbonates, polyamides, polyimides, polyurethanes, phenolics, polyamines, amino-epoxy resins, polyesters, silicones, cellulose based polymers, polysaccharides, or combinations thereof. In some embodiments, the polymeric material is a copolymer prepared using a comonomer having a complementary functional group capable of reacting with a group $X^1$ in compounds according to Formula I. For example, the comonomer can contain a carboxy, mercapto, hydroxy, amino, or alkoxysilyl group.

Suitable glass and ceramic substrate materials can include, for example, sodium, silicon, aluminum, lead, boron, phosphorous, zirconium, magnesium, calcium, arsenic, gallium, titanium, copper, or combinations thereof. Glasses typically include various types of silicate containing materials.

In some embodiments, the substrate includes a layer of diamond-like glass as disclosed in International Patent Application WO 01/66820 A1, the disclosure of which is incorporated herein by reference in its entirety. The diamond-like glass is an amorphous material that includes carbon, silicon, and one or more elements selected from hydrogen, oxygen, fluorine, sulfur, titanium, or copper. Some diamond-like glass materials are formed from a tetramethysilane precursor using a plasma process. A hydrophobic material can be produced that is further treated in an oxygen plasma to control the silanol concentration on the surface.

Diamond-like glass can be in the form of a thin film or in the form of a coating on another layer or material in the substrate. In some applications, the diamond-like glass can be in the form of a thin film having at least 30 weight percent carbon, at least 25 weight percent silicon, and up to 45 weight percent oxygen. Such films can be flexible and transparent. In some embodiments, the diamond-like glass is the outer layer of a multilayer substrate. In a specific example, the second layer (e.g., support layer) of the substrate is a polymeric material and the first layer is a thin film of diamond-like glass. The tethering group is attached to the surface of the diamond-like glass.

In some multilayer substrates, the diamond like glass is deposited on a layer of diamond-like carbon. For example, the second layer (e.g., support layer) is a polymeric film having a layer of diamond-like carbon deposited on a surface. A layer of diamond-like glass is deposited over the diamond-like carbon layer. The diamond-like carbon can, in some embodiments, function as a tie layer or primer layer between a polymeric layer and a layer of diamond-like glass in a multilayer substrate. For example, the multilayer substrate can include a polyimide or polyester layer, a layer of diamond-like carbon deposited on the polyimide or polyester, and a layer of diamond-like glass deposited on the diamond-like carbon. In another example, the multilayer substrate includes a stack of the layers arranged in the following order: diamond-like glass, diamond-like carbon, polyimide or polyester, diamond-like carbon, and diamond-like glass.

Diamond-like carbon films can be prepared, for example, from acetylene in a plasma reactor. Other methods of preparing such films are described U.S. Pat. Nos. 5,888,594 and 5,948,166 as well as in the article M. David et al., *AIChE Journal*, 37 (3), 367-376 (March 1991), the disclosures of which are incorporated herein by reference.

Suitable metals, metal oxides, or hydrated metal oxides for substrates can include, for example, gold, silver, platinum, palladium, aluminum, copper, chromium, iron, cobalt, nickel, zinc, and the like. The metal-containing material can be alloys such as stainless steel, indium tin oxide, and the like. In some embodiments, a metal-containing material is the top layer of a multilayer substrate. For example, the substrate can have a polymeric second layer and a metal containing first layer. In one example, the second layer is a polymeric film and the first layer is a thin film of gold. In other examples, a multilayer substrate includes a polymeric film coated with a titanium-containing layer and then coated with a gold-containing layer. That is, the titanium layer can function as a tie layer or a primer layer for adhering the layer of gold to the polymeric film.

In other examples of a multilayer substrate, a silicon support layer is covered with a layer of chromium and then with a layer of gold. The chromium layer can improve the adhesion of the gold layer to the silicon layer.

The surface of the substrate typically includes a group capable of reacting with a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group. That is, the substrate includes a group capable of reacting with the group $X^1$ in compounds of Formula I (i.e., the substrate includes a complementary functional group to the group $X^1$). Substrates can include a support material that is treated to have an outer layer that includes a complementary functional group. The substrate can be prepared from any solid phase material known to have groups capable of reacting with $X^1$ and is not limited to the following examples of suitable materials.

A carboxy group or a halocarbonyl group can react with a substrate having a hydroxy group to form a carbonyloxy-containing attachment group. Examples of substrate materials having hydroxy groups include, but are not limited to, polyvinyl alcohol, corona-treated polyethylene, hydroxy substituted esters of polymethacrylates, hydroxy substituted esters of polyacrylates, and a polyvinyl alcohol coating on a support material such as glass or polymer film.

A carboxy group or a halocarbonyl group can also react with a substrate having a mercapto group to form a carbonylthio-containing attachment group. Examples of substrate materials having a mercapto group include, but are not limited to, mercapto substituted esters of polyacrylates, mercapto substituted esters of polymethacrylates, and glass treated with a mercaptoalkylsilane.

Additionally, a carboxy group or a halocarbonyl group can react with a primary aromatic amino group, a secondary aromatic amino group, or a secondary aliphatic amino group to form a carbonylimino-containing attachment group. Examples of substrate materials having aromatic primary or secondary amino groups include, but are not limited to, polyamines, amine substituted esters of polymethacrylate, amine substituted esters of polyacrylate, polyethylenimines, and glass treated with an aminoalkylsilane.

A halocarbonyloxy group can react with a substrate having a hydroxy group to form an oxycarbonyloxy-containing attachment group. Examples of substrate materials having hydroxy groups include, but are not limited to, polyvinyl alcohol, corona-treated polyethylene, hydroxy substituted esters of polymethacrylates, hydroxy substituted esters of polyacrylates, and a polyvinyl alcohol coating on a support material such as glass or polymer film.

A halocarbonyloxy group can also react with a substrate having a mercapto group to form an oxycarbonylthio-containing attachment group. Examples of substrate materials having a mercapto group include, but are not limited to, mercapto substituted esters of polymethacrylates, mercapto substituted esters of polyacrylates, and glass treated with a mercaptoalkylsilane.

Additionally, a halocarbonyloxy group can react with a substrate having a primary aromatic amino group, a secondary aromatic amino group, or a secondary aliphatic amino group to form an oxycarbonylimino-containing attachment group. Examples of substrate materials having aromatic primary or secondary amino groups include, but are not limited to, polyamines, amine substituted esters of polymethacrylate, amine substituted esters of polyacrylate, polyethylenimines, and glass treated with an aminoalkylsilane.

A cyano group can react with a substrate having an azido group to form a tetrazinediyl-containing attachment group. Examples of substrates having azido groups include, but are not limited to, a coating of poly(4-azidomethylstyrene) on a glass or polymeric support. Suitable polymeric support materials include polyesters, polyimides, and the like.

A hydroxy group can react with a substrate having isocyanate group to form an oxycarbonylimino-containing attachment group. Suitable substrates having isocyanate groups include, but are not limited to, a coating of 2-isocyanatoethylmethacrylate polymer on a support material. Suitable support materials include glass and polymeric materials such as polyesters, polyimides, and the like.

A hydroxy group can also react with a substrate having a carboxy, carbonyloxycarbonyl, or halocarbonyl to form a carbonyloxy-containing attachment group. Suitable substrates include, but are not limited to, a coating of acrylic acid polymer or copolymer on a support material or a coating of a methacrylic acid polymer or copolymer on a support material. Suitable support materials include glass and polymeric materials such as polyesters, polyimides, and the like. Other suitable substrates include copolymers of polyethylene with polyacrylic acid, polymethacrylic acid, or combinations thereof.

A mercapto group can react with a substrate having isocyanate groups. The reaction between a mercapto group and an isocyanate group forms a thiocarbonylimino-containing attachment group. Suitable substrates having isocyanate groups include, but are not limited to, a coating of 2-isocyanatoethylmethacrylate copolymer on a support material. Suitable support materials include glass and polymeric materials such as polyesters, polyimides, and the like.

A mercapto group can also react with a substrate having a halocarbonyl group to form a carbonylthio-containing attachment group. Substrates having halocarbonyl groups include, for example, chlorocarbonyl substituted polyethylene.

A mercapto group can also react with a substrate having a halocarbonyloxy group to form an oxycarbonlythio-containing attachment group. Substrates having halocarbonyl groups include chloroformyl esters of polyvinyl alcohol.

Additionally, a mercapto group can react with a substrate having an ethylenically unsaturated group to form a thioether-containing attachment group. Suitable substrates having an ethylenically unsaturated group include, but are not limited to, polymers and copolymers derived from butadiene.

An isocyanate group can react with a substrate having a hydroxy group to form a oxycarbonylimino-containing attachment group. Examples of substrate materials having hydroxy groups include, but are not limited to, polyvinyl alcohol, corona-treated polyethylene, hydroxy substituted esters of polymethacrylates or polyacrylates, and a polyvinyl alcohol coating on glass or polymer film.

An isocyanate group can also react with a mercapto group to form a thiocarbonylimino-containing attachment group. Examples of substrate materials having a mercapto group include, but are not limited to, mercapto substituted esters of polymethacrylates or polyacrylates and glass treated with a mercaptoalkylsilane.

Additionally, an isocyanate group can react with a primary aromatic amino group, a secondary aromatic amino group, or a secondary aliphatic amino group to form a urea-containing attachment group. Suitable substrates having a primary or secondary aromatic amino group include, but are not limited to, polyamines, polyethylenimines, and coatings of an aminoalkylsilane on a support material such as glass or on a polymeric material such as a polyester or polyimide.

An isocyanate group can also react with a carboxy to form an O-acyl carbamoyl-containing attachment group. Suitable substrates having a carboxylic acid group include, but are not limited to, a coating of an acrylic acid polymer or copolymer or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A halosilyl group, an alkoxysilyl group, or an acyloxysilyl group can react with a substrate having a silanol group to form a disiloxane-containing attachment group. Suitable substrates include those prepared from various glasses, ceramic materials, or polymeric material. These groups can also react with various materials having metal hydroxide groups on the surface to form a silane-containing linkage. Suitable metals include, but are not limited to, silver, aluminum, copper, chromium, iron, cobalt, nickel, zinc, and the like. In some embodiments, the metal is stainless steel or another alloy. Polymeric material can be prepared to have silanol groups. For example, commercially available monomers with silanol groups include 3-(trimethoxysilyl)propyl methacrylate and 3-aminoproplytrimethoxysilane available from Aldrich Chemical Co., Milwaukee, Wis.

An azido group can react, for example, with a substrate having carbon-carbon triple bond to form triazolediyl-containing attachment groups. An azido group can also react with a substrate having nitrile groups to form a tetrazenediyl-containing attachment group. Substrates having nitrile groups include, but are not limited to, coatings of polyacrylonitrile on a support material such as glass or a polymeric material. Suitable polymeric support material includes polyesters and polyimides, for example. Other suitable substrates having nitrile groups include acrylonitrile polymers or copolymers and 2-cyanoacrylate polymers or copolymers.

An azido group can also react with a strained olefinic group to form a triazolediyl-containing attachment group. Suitable substrates have a strained olefinic group include coatings that have pendant norbornenyl functional groups. Suitable support materials include, but are not limited to, glass and polymeric materials such as polyesters and polyimides.

An aziridinyl group can react with a mercapto group to form a aminoalkylthioether-containing attachment group. Examples of substrate materials having a mercapto group include, but are not limited to, mercapto substituted esters of polymethacrylates or polyacrylates and glass treated with a mercaptoalkylsilane.

Additionally, an aziridinyl group can react with a carboxy group to form a aminoalkyloxycarbonyl-containing attachment group. Suitable substrates having a carboxy include, but are not limited to, a coating of a acrylic acid polymer or copolymer, or a coating of a methacrylic acid polymer or copolymer on a glass or polymeric support. Copolymers include, but are not limited to, copolymers that contain polyethylene and polyacrylic acid or polymethacrylic acid. Suitable polymeric support materials include polyesters, polyimides, and the like.

A haloalkyl group can react, for example, with a substrate having a tertiary amino group to form a quaternary ammonium-containing attachment group. Suitable substrates having a tertiary amino group include, but are not limited to, polydimethylaminostyrene or polydimethylaminoethylmethacrylate.

Likewise, a tertiary amino group can react, for example, with a substrate having a haloalkyl group to form a quaternary ammonium-containing attachment group. Suitable substrates having a haloalkyl group include, for example, coatings of a haloalkylsilane on a support material. Support materials can include, but are not limited to, glass and polymeric materials such as polyesters and polyimides.

A primary aromatic amino or a secondary aromatic amino group can react, for example, with a substrate having an isocyanate group to form a oxycarbonylimino-containing attachment group. Suitable substrates having isocyanate groups include, but are not limited to, a coating of a 2-isocyanatoethylmethacrylate polymer or copolymer on a glass or polymeric support. Suitable polymeric supports include polyesters, polyimides, and the like.

A primary aromatic amino or a secondary aromatic amino group can also react with a substrate containing a carboxy or halocarbonyl group to form a carbonylimino-containing attachment group. Suitable substrates include, but are not limited to, acrylic or methacrylic acid polymeric coatings on a support material. The support material can be, for example, glass or a polymeric material such as polyesters or polyimides. Other suitable substrates include copolymers of polyethylene and polymethacrylic acid or polyacrylic acid.

A disulfide or an alkyl disulfide group can react, for example, with a metal surface to form a metal sulfide-containing attachment group. Suitable metals include, but are not limited to gold, platinum, palladium, nickel, copper, and chromium. The substrate can also be an alloy such an indium tin oxide or a dielectric material.

A benzotriazolyl can react, for example, with a substrate having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

A phosphono, phosphoroamido, or phosphate can react, for example, with a substrate having a metal or metal oxide surface. Suitable metals or metal oxides include, for example, silver, aluminum, copper, chromium, iron, cobalt, nickel, zinc, and the like. The metals or metal oxides can include alloys such as stainless steel, indium tin oxide, and the like.

An ethylenically unsaturated group can react, for example, with a substrate having an alkyl group substituted with a mercapto group. The reaction forms a heteroalkylene-containing attachment group. Suitable substrates include, for example, mercapto-substituted alkyl esters of polyacrylates or polymethacrylates.

An ethylenically unsaturated group can also react with a substrate having a silicon surface, such as a silicon substrate formed using a chemical vapor deposition process. Such silicon surfaces can contain —SiH groups that can react with the ethylenically unsaturated group in the presence of a platinum catalyst to form an attachment group with Si bonded to an alkylene group.

Additionally, an ethylenically unsaturated group can react with a substrate having a carbon-carbon double bond to form an alkylene-containing attachment group. Such substrates include, for example, polymers derived from butadiene.

The compounds of Formula I can undergo a self-assembly process when contacted with a substrate. As used herein, the term "self-assembly" refers to process in which a material can spontaneously form a monolayer of substrate-attached tethering groups when contacted with a substrate. For example, compounds having a disulfide or alkyl disulfide group for $X^1$ can undergo a self-assembly process when exposed to a gold substrate. As another example, compounds having a halosilyl group for $X^1$ can undergo a self-assembly process when exposed to a diamond-like glass or glass substrate.

In one embodiment, Formula II can represent the articles of the invention:

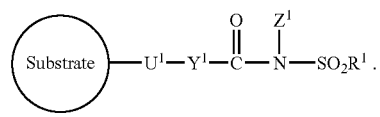
II

Formula II represents a tethering group attached to a substrate. The tethering group is derived from a compound according to Formula I. The group $U^1$ is the attachment group formed by reaction of $X^1$ in a compound according to Formula I with a complementary functional group on the surface of a substrate. The groups $Y^1$ and $R^1$ are the same as previously defined for Formula I. That is, the article includes:

a substrate; and a substrate-attached tethering group that includes a reaction product of a complementary functional group G on a surface of the substrate with a compound of Formula I

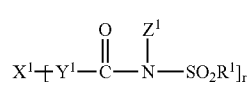
I wherein

X$^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, or phosphato;

Y$^1$ is a single bond or a divalent group selected from an alkylene, heteroalkylene, arylene, carbonyl, carbonyloxy, carbonylimino, oxy, thio, —NR$^d$— where R$^d$ is hydrogen or alkyl, or combinations thereof;

Z$^1$ is an alkyl, aryl, or —(CO)R$^a$ wherein R$^a$ together with R$^1$ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

R$^1$ is an alkyl, fluoroalkyl, chloroalkyl, aryl, NR$^b$R$^c$ wherein R$^b$ and R$^c$ are each an alkyl group or taken together with the nitrogen atom to which they are attached form a four to eight membered cyclic group having a nitrogen heteroatom, or R$^1$ together with R$^a$ and the groups to which they are attached form the four to eight membered heterocyclic or heterobicyclic group that can be fused to the optional aromatic group, optional saturated or unsaturated cyclic group, or optional saturated or unsaturated bicyclic group;

r is equal to 1 when X$^1$ is a monovalent group or equal to 2 when X$^1$ is a divalent group; and G is a group capable of reacting with X$^1$ to form an ionic bond, covalent bond, or combinations thereof. The tethering group can be unsubstituted or substituted with a halo, alkyl, alkoxy, or combinations thereof.

Formula II shows only one tethering group attached to the substrate; however, more than one tethering group can be attached to the substrate if there are more than one reactive group G on the substrate. Further, the substrate can have excess G groups on the surface of the substrate that have not reacted with a tethering compound.

Groups on a substrate (i.e., groups G) capable of reacting with X$^1$ groups in compounds according to Formula I include, but are not limited to, hydroxy, mercapto, primary aromatic amino group, secondary aromatic amino group, secondary aliphatic amino group, azido, carboxy, carbonyloxycarbonyl, isocyanate, halocarbonyl, halocarbonyloxy, silanol, and nitrile.

The attachment of tethering groups to the surface of a substrate (i.e., formation of the substrate-attached tethering groups of Formulas II) can be detected using techniques such as, for example, contact angle measurements of a liquid on the substrate before and after attachment of a tethering group derived from Formula I (e.g., the contact angle can change upon attachment of a tethering group to the surface of a substrate), ellipsometry (e.g., the thickness of the attached layer can be measured), time-of-flight mass spectroscopy (e.g., the surface concentration can change upon attachment of a tethering group to a substrate), and Fourier Transform Infrared Spectroscopy (e.g., the reflectance and absorbance can change upon attachment of a tethering group to a substrate).

In other embodiments of articles of the invention, the N-sulfonylaminocarbonyl group in the tethering group has reacted with an amine-containing material. A carbonylimino-containing connector group is formed resulting in the immobilization of an amine-containing material to the substrate. The amine-containing material can react with a N-sulfonylaminocarbonyl group of the substrate-attached tethering group of Formula II. In some embodiments, the amine-containing materials are biomolecules such as, for example, amino acid, peptide, DNA, RNA, protein, enzyme, organelle, immunoglobin, or fragments thereof. In other embodiments, the amine-containing material is a non-biological amine such as an amine-containing analyte.

The amine-containing material (H$_2$N-T) can react with the substrate-attached tethering group of Formula II by a nucleophilic substitution reaction to produce a substrate immobilized amine-containing material of Formula III:

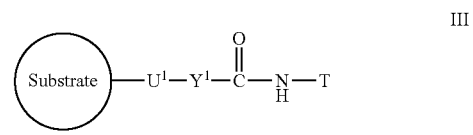

where U$^1$ is the attachment group formed by reacting X$^1$ of a compound according to Formula I with a complementary functional group on the surface of the substrate; T is the remainder of the amine-containing material; and Y$^1$ and R$^1$ are the same as previously defined for Formulas I and II. H$_2$N-T is any suitable primary amine-containing material. In some embodiments, H$_2$N-T is a biomolecule.

The presence of the immobilized amine can be determined, for example, using mass spectroscopy, contact angle measurement, infrared spectroscopy, and ellipsometry. Additionally, various immunoassays and optical microscopic techniques can be used if the amine-containing material is a biologically active material.

Other materials can be bound to the amine-containing material. For example, a complementary RNA or DNA fragment can hybridize with an immobilized RNA or DNA fragment. In another example, an antigen can bind to an immobilized antibody or an antibody can bind to an immobilized antigen. In a more specific example, a bacterium such as *Staphylococcus aureus* can bind to an immobilized biomolecule.

Method of Immobilizing Amine-Containing Material to a Substrate

Another aspect of the invention provides methods for immobilizing an amine-containing material to a substrate. The method involves preparing a substrate-attached tethering group by reacting a complementary functional group on the surface of the substrate with the substrate-reactive group X$^1$ in compounds of Formula I; and reacting a N-sulfonylaminocarbonyl group of the substrate-attached tethering group with an amine-containing material to form a carbonylimino-containing connector group between the substrate and the amine-containing material.

In one embodiment, the method of immobilizing an amine-containing material to a substrate is shown in Reaction Scheme B for a monovalent X$^1$.

Reaction Scheme B

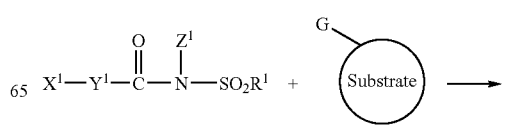

-continued

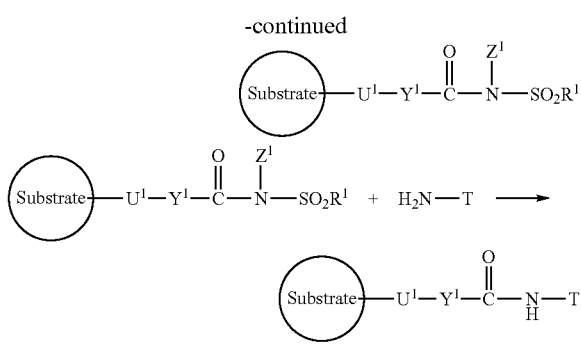

where $U^1$ is the attachment group formed by reacting $X^1$ in compound of Formula I with a complementary functional group G on the surface of the substrate; T is the remainder of the amine-containing material, (i.e., the group T represents all of the amine-containing material exclusive of the amine group). The groups $Y^1$ and $R^1$ are the same as previously defined for Formula I. $H_2N$-T is any suitable amine-containing material. In some embodiments, $H_2N$-T is a biomolecule. The method involves:

selecting a compound of Formula I

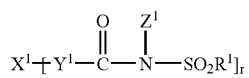

I wherein $X^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, phosphato, or ethylenically unsaturated group;

$Y^1$ is a single bond or a divalent group selected from an alkylene, heteroalkylene, arylene, carbonyl, carbonyloxy, carbonylimino, oxy, thio, —$NR^d$— where $R^d$ is hydrogen or alkyl, or combinations thereof;

$Z^1$ is an alkyl, aryl, or —$(CO)R^a$ wherein $R^a$ together with $R^1$ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

$R^1$ is an alkyl, fluoroalkyl, chloroalkyl, aryl, $NR^bR^c$ wherein $R^b$ and $R^c$ are each an alkyl group or taken together with the nitrogen atom to which they are attached form a four to eight membered cyclic group, or $R^1$ together with $R^a$ and the groups to which they are attached form the four to eight membered heterocyclic or heterobicyclic group that can be fused to the optional aromatic group, optional saturated or unsaturated cyclic group, or optional saturated or unsaturated bicyclic group;

r is equal to 1 when $X^1$ is a monovalent group or equal to 2 when $X^1$ is a divalent group; and said compound of Formula I is unsubstituted or substituted with a halo, alkyl, alkoxy, or combinations thereof;

providing a substrate having a complementary functional group capable of reacting with $X^1$;

preparing a substrate-attached tethering group by reacting $X^1$ with the complementary functional group on the substrate resulting in an ionic bond, covalent bond, or combinations thereof, and reacting a N-sulfonylaminocarbonyl group of the substrate-attached tethering group with an amine-containing material to form a carbonylimino-containing connector group. That is, the connector group is a divalent group of formula —$U^1$—$Y^1$—(CO)—NH— (the divalent group between the substrate and the group T in Formula III). The attachment group is part of the connector group.

Uses

The compounds of the invention can be used, for example, for immobilizing amine-containing material. In some embodiments, the amine-containing material is an amine-containing analyte. In other embodiments, the amine-containing materials are biomolecules such as, for example, amino acids, peptides, DNA, RNA, protein, enzymes, organelles, immunoglobins, or fragments thereof. Immobilized biological amine-containing materials can be useful in the medical diagnosis of a disease or of a genetic defect. The immobilized amine-containing materials can also be used for biological separations or for detection of the presence of various biomolecules. Additionally, the immobilized amine-containing materials can be used in bioreactors or as biocatalysts to prepare other materials. The substrate-attached tethering groups can be used to detect amine-containing analytes.

Biological amine-containing materials often can remain active after attachment to the substrate (i.e., the articles according to Formula III can include biologically active amine-containing materials immobilized to the substrate). For example, an immobilized antibody can bind with antigen or an immobilized antigen can bind to an antibody. An amine-containing material can bind to a bacterium. In a more specific example, the immobilized amine-containing material can bind to a *Staphylococcus aureus* bacterium (e.g., the immobilized amine-containing material can be a biomolecule that has a portion that can specifically bind to the bacterium).

The articles prepared by attaching the compounds of the invention to a substrate typically have improved hydrolytic stability compared to previously known articles prepared using a tethering compound that is a derivative of N-hydroxysuccinimide. Because of the hydrolytic stability, the compounds and the substrate-attached tethering groups of the invention can typically be used in aqueous systems.

When an amine-containing material reacts with a N-sulfonylaminocarbonyl group, a carbonylimino-containing connector group is formed that results in the immobilization of the amine-containing material to the substrate (i.e., substrate immobilized amine-containing materials according to Formulas III). The rate of reaction of amine-containing materials with the N-sulfonylaminocarbonyl groups of the substrate-attached tethering groups is typically faster than the rate of hydrolysis of the N-sulfonylaminocarbonyl group. That is, immobilization of amine-containing materials occurs at a faster rate than the hydrolysis reactions. The amine-containing materials are not easily displaced once immobilization to a substrate has occurred due to the formation of a covalent carbonylimino bond.

EXAMPLES

Unless otherwise noted, all solvents and chemical reagents were or can be obtained from Aldrich Chemical Co., Milwaukee, Wis.

Gold-coated silicon substrates were obtained from Wafer-Net, Inc., San Jose, Calif. and were 150 mm prime-grade N-type silicon wafers onto one side of which metal was deposited by reactive sputtering. The wafers were first treated to deposit, by reactive sputtering, a layer of chromium and were then treated to deposit, by reactive sputtering, a layer of gold. The thickness of the gold layer was 5000 Angstroms.

N-phenyltrifluoromethanesulfonamide can be obtained from Interchim, Montlucon, France.

Aqueous buffer solutions were obtained from Sigma Aldrich Co., Milwaukee, Wis. or were prepared by known methods.

HSA and conjugated and unconjugated IgG (i.e., Immunoglobulin G) were obtained from Jackson ImmunoResearch Laboratories, Inc., West Grove, Pa.

The IR and $^1$H NMR spectra of each product formed in the Preparative Examples and Examples were consistent with the assigned structure.

Glossary

As used herein:

"CHES buffer" refers to an aqueous solution of 2-(cyclohexylamino)ethanesulfonic acid;

"DLC" refers to a diamond-like carbon coating prepared as described;

"DLG" refers to a diamond-like glass coating prepared as described;

"DMF" refers to N,N-dimethylformamide;

"ELISA" refers to enzyme-linked immunoabsorbent assay;

"FITC-ALBUMIN" refers to fluorescein-labeled bovine serum albumin, which was obtained as a 2 mg/mL solution in bicarbonate buffer from Sigma-Aldrich Corp., St. Louis, Mo.;

"HSA" refers to human serum albumin;

"SA-HRP" refers to streptavidin conjugated with horseradish peroxidase, which was obtained from Jackson ImmunoResearch Laboratories, Inc., West Grove, Pa.;

"ABTS" refers to 2,2'-azino-di-(3-ethylbenzthiazoline-6-sulfonate), which was obtained in kit form from KPL Inc., Gaithersburg, Md.;

"PBS" refers to phosphate buffered saline which has a pH of about 7.4;

"SDS" refers to sodium dodecyl sulfate; and

"TWEEN 20" refers to polyoxyethylene(20) sorbitan monolaurate.

Methods

Contact Angle Measurements

Advancing and receding contact angles of deionized water were measured in air at room temperature using a Model 100 goniometer (available from Rame-Hart, Inc., Mountain Lakes, N.J.).

Ellipsometry

Ellipsometric determination of monolayer thickness was carried out using a Model AutoEL ellipsometer (available from Rudolph Technologies, Inc., Flanders, N.J.) at a wavelength of 6320 Angstroms and at an angle of incidence of 70 degrees. For each substrate, ellipsometric constants were determined by extrapolation of self assembled monolayers of 1-mercaptohexadecane, 1-mercaptododecane, and 1-mercaptooctane. The ellipsometric thicknesses of the monolayers were estimated by using a three-layer model and by assuming the refractive index of 1.46 for the monolayer.

Preparative Example 1

Preparation of N-methyltrifluoromethanesulfonamide

A weighed pressure reactor (available from Parr Instrument Co., Moline, Ill.) is charged with dichloromethane (100 mL) and is then cooled using liquid nitrogen. Methylamine is introduced from a cylinder via a stainless steel tube that is connected to a valve on the reactor. The reactor is periodically weighed, and methylamine is added until 20 g have been added. Trifluoromethanesulfonylfluoride is then introduced into the reactor from a cylinder via a stainless steel tube until 97.9 g have been added. The pressure reactor is then sealed and is placed in a motorized rocker and is rocked and allowed to warm to room temperature. After a period of about 6 hours after the reactor reaches room temperature, it is slowly vented to the atmosphere by opening the valve. The product residue is washed with 10 weight percent aqueous HCl and the organic phase is then dried over $MgSO_4$. The mixture is filtered and the solvent is removed from the filtrate using a rotary evaporator to afford the product.

Preparative Example 2

Preparation of

A solution of KOH (2.7 g) in ethanol (30.8 g) was magnetically stirred at room temperature. 11-Mercaptoundecanoic acid (5.0 g) was added slowly to the KOH solution. After the addition was complete, a solution of iodine (2.9 g) in ethanol (62.2 g) was added and the mixture was stirred for approximately one hour longer. The mixture was then poured into 1N aqueous HCl and the precipitated solid was isolated by filtration. The solid was washed with deionized water and was dried in air to afford 5.0 g of product.

Preparative Example 3

Preparation of

A mixture of the carboxy-containing product from Preparative Example 2 (2.0 g), thionyl chloride (1.15 g), and methylene chloride (12.6 g) was stirred and heated at reflux under a nitrogen atmosphere in a round bottom flask that was fitted with a magnetic stir bar, a reflux condenser, and a heating mantle. After 6 hours, the mixture was cooled to room temperature and the volatile components were removed using a rotary evaporator to afford the product.

Preparative Example 4

Preparation of

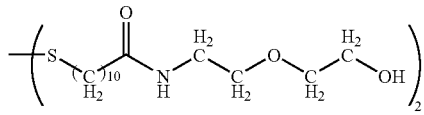

The chlorocarbonyl-containing product of Preparative Example 3 (10.9 g) dissolved in methylene chloride (30 mL) was added slowly to a magnetically stirred solution of 2-(2-aminoethoxy)ethanol (9.7 g) and N,N-diisopropylethylamine (6.27 g) in methylene chloride (37 mL) within a round bottom flask. During the addition, the flask was cooled in an ice bath. After the addition was complete, the mixture became viscous. An attempt to extract the mixture with deionized water resulted in a partial emulsion. The volatile components were removed using a rotary evaporator and the remaining mixture was heated to boiling, which resulted in the precipitation of a white solid. This solid was filtered and was then dissolved in acetonitrile (250 mL). The acetonitrile solution was stirred and was concentrated by directing a stream of nitrogen gas onto the surface of the solution. The resultant white crystals were isolated by filtration and were dried overnight under a stream of nitrogen gas to afford 12.6 g of product.

Preparative Example 5

Preparation of

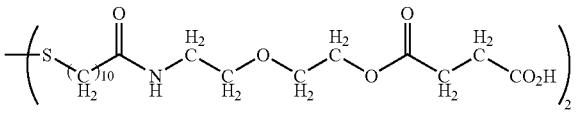

A mixture of the hydroxy-containing product of Preparative Example 4 (3.0 g), succinic anhydride (1.1 g) and triethylamine (1.15 g) was heated within an Erlenmeyer flask for 6 hours. The mixture was allowed to cool to room temperature and methyl alcohol was added to the flask. The product formed a dark thick liquid that was not miscible with the methyl alcohol. The methyl alcohol was decanted away from the dark residue and the product was then recrystallized from acetonitrile to afford 3.43 g of product.

Preparative Example 6

Preparation of

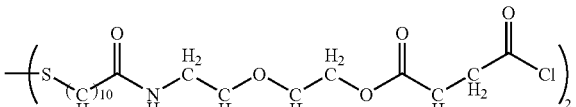

A mixture of the carboxy-containing product of Preparative Example 5 (0.5 g), thionyl chloride (0.15 g), DMF (1 drop) and dichloromethane (2.0 g) was magnetically stirred overnight. The volatile components were removed using a rotary evaporator to afford the product (0.52 g).

Preparative Example 7

Preparation of

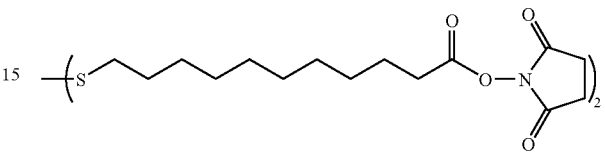

A mixture of the carboxy-containing product of Preparative Example 2 (2.0 g), thionyl chloride (1.15 g), and methylene chloride (12.6 g) was heated under reflux within a round bottom flask that was fitted with a reflux condenser, a hose adapter connected to a source of nitrogen gas, and a heating mantle. After 6 hours, the mixture was concentrated to dryness using a rotary evaporator. To the flask was then added methylene chloride (12.6 g) and to this solution was added dropwise a mixture of N-hydroxysuccinimide (1.11 g) and pyridine (0.8 g). The mixture was stirred at room temperature overnight and then the volatile materials were removed using a rotary evaporator. The residue was recrystallized from isopropyl alcohol to afford 2.91 g of product.

Preparative Example 8

Preparation of a Multilayer Substrate of DLG-DLC-polyimide-DLC-DLG

A Model 2480 parallel-plate capacitively coupled reactive ion etcher (obtained from PlasmaTherm, St. Petersburg, Fla.) was used to deposit a diamond-like glass (DLG) coating using a tetramethylsilane plasma onto a diamond-like carbon coating (DLC). The DLC coating was deposited using an acetylene plasma with the Model 2480 reactive ion etcher onto a polyimide film.

An approximately 20 cm by 30 cm sample of polyimide film (available under the trade designation "KAPTON E" from E.I. du Pont de Nemours & Co., Wilmington, Del.) was affixed to the powered electrode of the ion etcher using 3M 811 Adhesive Tape from 3M Company, St. Paul, Minn. The ion etcher chamber was closed and the chamber was pumped to a pressure of 0.67 Pa (0.005 Torr). Oxygen gas was introduced into the chamber at a flow rate of 500 standard $cm^3$ per minute, and the pressure of the chamber was maintained at 6.7 Pa (0.050 Torr). Plasma was ignited and was sustained at a power of 2000 W for 15 seconds. The oxygen gas flow was then terminated and the chamber was allowed to pump to a pressure of 0.67 Pa (0.005 Torr). Acetylene gas was then introduced into the chamber at a flow rate of 200 standard $cm^3$ per minute, and the pressure of the chamber was maintained at 2 Pa (0.015 Torr). Plasma was ignited and was sustained at a power of 1600 W for 10 seconds. The flow of acetylene gas was then terminated and the chamber was allowed to pump to a pressure of 0.67 Pa (0.005 Torr).

Oxygen gas was again introduced into the chamber at a flow rate of 500 standard $cm^3$ per minute and, the pressure of the chamber was maintained at 20 Pa (0.15 Torr). Plasma was ignited and was sustained at a power of 300 W for 10 seconds. With the oxygen gas flow rate maintained at 500 standard cm$^3$ per minute, tetramethylsilane gas was introduced into the chamber at a flow rate of 150 standard cm$^3$ per minute. The chamber pressure was maintained at 20 Pa (0.15 Torr). Plasma was ignited and was sustained at a power of 300 W for 12 seconds. The flow of tetramethylsilane gas was terminated. After a period of 1 minute, with both the flow of oxygen gas and the chamber pressure of 20 Pa (0.15 Torr) maintained, plasma was ignited and was sustained at a power of 300W for 20 seconds. The flow of oxygen gas was then terminated and the chamber pressure was allowed to pump to a pressure of 0.67 Pa (0.005 Torr). The chamber was then opened to the atmosphere and the sample was removed from the powered electrode, turned so that the DLG coating faced the electrode, and was again affixed to the electrode. The sequence of plasma treatments was repeated to provide a sample of polyimide with sequential layers of DLC and DLG on each side.

Preparative Example 9

Preparation of a Multilayer Substrate of Glass-DLC-DLG

A 25 mm by 75 mm glass microscope slide (available as "MICRO SLIDES SELECTED" from VWR Scientific, West Chester, Pa.) was treated in a plasma chamber according to the method of Preparative Example 8 to sequentially deposit layers of DLC and DLG onto one side of the glass microscope slide.

Preparative Example 10

Preparation of a Multilayer Substrate of Polyimide-Titanium-Gold

Sequential layers of titanium and gold were deposited by electron beam evaporation onto polyimide film. A 10 cm by 15 cm sample of polyimide film (available under the trade designation "KAPTON E" from E. I. Du Pont de Nemours & Co., Wilmington, Del.) was affixed to the plate of the planetary system in a Model Mark 50 high vacuum deposition system (available from CHA Industries, Fremont, Calif.) using metal stationery binder clips. The chamber was evacuated for approximately 2 hours, during which time the chamber pressure was reduced to approximately $6.7 \times 10^{-4}$ Pa ($5 \times 10^{-6}$ mm Hg). Titanium metal was deposited at a rate of approximately 5 Angstroms per second to a total thickness of approximately 200 Angstroms. Deposition of titanium was then terminated and the system was allowed to cool for approximately 30 minutes. Gold metal was then deposited onto the titanium layer at a rate of approximately 1 Angstrom per second to a total thickness of approximately 2000 Angstroms. Deposition of gold was then terminated and the system was allowed to cool for approximately 30 minutes before the chamber pressure was raised to atmospheric pressure and the samples were removed.

Preparative Example 11

Attachment of an N-acyloxysuccinimide Containing Tethering Group to Gold-Coated Silicon Substrate A 250-micromolar solution of the N-acyloxysuccinimide-containing product of Preparative Example 7 in acetone was prepared. A 1 cm by 1 cm portion of a gold-coated silicon wafer was immersed in the solution for 30 minutes, after which time it was removed and was rinsed sequentially with ethanol and methanol and was then dried by directing a stream of nitrogen gas over the treated gold surface for approximately 1 minute. The ellipsometric thickness was determined to be 17 Angstroms and the static advancing contact angle of deionized water on the surface was determined to be 50 degrees.

Preparative Example 12

Preparation of Acid Chloride Functionalized poly(methylmethacrylate-co-methacrylic acid) Beads Poly(methylmethacrylate-co-methacrylic acid) beads (available under the trade designation "MCI GEL CQK31P" from Mitsubishi Chemical Corp., Tokyo, Japan) (20 g) were combined with cyclohexane (66 g) and thionyl chloride (8.3 g) in a round bottom flask fitted with a magnetic stir bar, a reflux condenser and a source of nitrogen gas. The mixture was heated under reflux for 6 hours, during which time nitrogen gas was slowly passed through the apparatus. The mixture was then allowed to cool to room temperature and filtered. The beads were washed with cyclohexane and were then dried under a stream of nitrogen gas overnight to afford the product.

Preparative Example 13

Preparation of Hydroxyl Functionalized poly(methylmethacrylate-co-methacrylic acid) Beads The acid chloride functionalized poly(methylmethacrylate-co-methacrylic acid) b beads of Preparative Example 12 (20.43 g) were combined with 2-(2-aminoethoxy)ethanol (40.0 g) in a round bottom flask fitted with a magnetic stir bar. The mixture was stirred overnight at room temperature and then the beads were filtered and washed with methanol. The beads were then dried under a stream of nitrogen gas overnight to afford the product.

Example 1

Preparation of

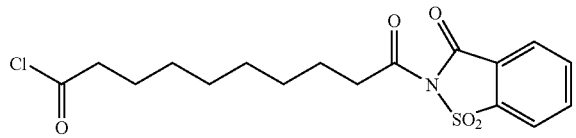

A mixture of dry sodium saccharin (10.25 g), dimethoxyethane (150 mL), and sebacoyl chloride (18.0 g) was stirred overnight at room temperature under a nitrogen atmosphere. The mixture was then filtered and filtrate was concentrated using a rotary evaporator. The product residue was triturated with a 10:1 (v/v) mixture of hexane and toluene and this mixture was cooled and then filtered. The filtered solid was dried to afford 22.1 g of product.

Example 2

Preparation of

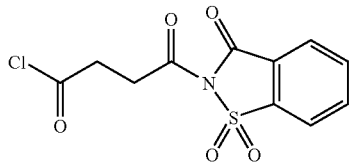

A mixture of sodium saccharin dihydrate (1.0 g) and toluene (approximately 15 mL) was magnetically stirred and boiled under reflux in a round bottom flask fitted with a Dean-Stark trap and a reflux condenser. After 6 hours, the mixture was allowed to cool to room temperature and the volatile components were removed using a rotary evaporator. The entire portion of this material was combined with dry acetone (5.6 g) and succinoyl chloride (2.57 g) in a round bottom flask. The mixture was magnetically stirred at room temperature for 30 minutes after which time it was filtered. The filtrate was concentrated using a rotary evaporator. The residue was then further concentrated by connecting the flask to a high vacuum pump using a hose adapter. The flask was heated to 75° C. using an oil bath while the flask was connected to the vacuum pump. After approximately 2 hours, the flask was allowed to cool to room temperature and was disconnected from the pump. The product residue was then triturated with toluene that resulted in the formation of a solid precipitate. The mixture was filtered and the solid was dried at room temperature to afford 1.0 g of product.

Example 3

Preparation of

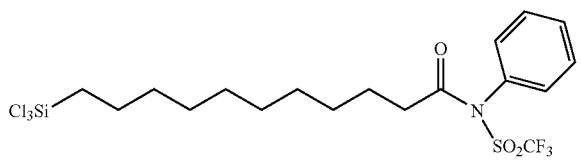

A solution of N-phenyltrifluoromethylsulfonamide (2.2 g) and N,N-diisopropylethylamine (1.3 g) in dry THF (25 mL) is added to a stirred solution of 10-undecenoyl chloride (2.0 g) in dry THF (25 mL). The solution is stirred overnight at room temperature and then the volatile components are removed using a rotary evaporator and then a high vacuum pump. A solution of this material is then made in methylene chloride (30 g) in 125 mL screw cap bottle. Platinum(0)-1,3-divinyl-1,1,3,3-tetramethyldisilane complex in xylenes is diluted with methylene chloride to a concentration of approximately 1.5 weight percent, and 3 drops of this solution are added to the bottle. The bottle is then sealed and is heated to 60° C. in a water bath. After 18 hours, the mixture is allowed to cool to room temperature and additional platinum complex solution (1 drop) is added. The bottle is again sealed and is heated at 60° C. for an additional 24 hours. The mixture is then cooled to room temperature and the volatile components are removed using a rotary evaporator to afford the product.

Example 4

Preparation of

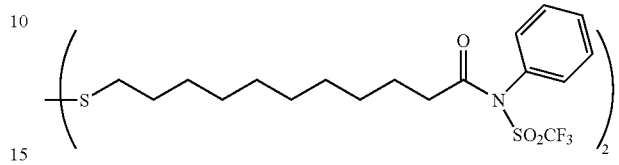

A solution of N-phenyltrifluoromethanesulfonamide (0.97 g) and N,N-diisopropylethylamine (0.58 g) in dry THF (3.9 g) was added to a stirred solution of the product of Preparative Example 3 (1.0 g) in dry THF (4.0 g) within a round bottom flask. This mixture was allowed to stir overnight. The volatile components were then removed using a rotary evaporator. The residue was dissolved in chloroform (40 mL) and was washed first with 0.1N aqueous HCl (40 mL) and then with saturated aqueous sodium chloride. The organic phase was dried over magnesium sulfate and was then filtered. The volatile components were removed using a rotary evaporator to afford 1.03 g of product.

Example 5

Preparation of

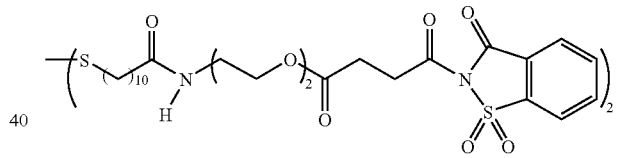

Solid sodium saccharin (0.38 g) was added at room temperature to a magnetically stirred solution of the chlorocarbonyl containing product of Preparative Example 6 (0.75 g) in dry acetone (4.1 g). After mixing overnight, the mixture was poured into deionized water in a beaker and the resultant solid was filtered and dried overnight in a vacuum oven at room temperature and 66.7 Pa (0.5 mm Hg) to afford 0.60 g of product.

Example 6

Preparation of

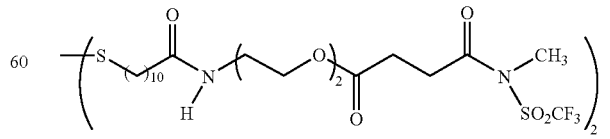

A solution of N-methyltrifluoromethanesulfonamide (0.203 g) and N,N-diisopropylethylamine (0.17 g) in THF (0.8 g) was slowly added to a stirred solution of the chlorocarbonyl containing product of Preparative Example 6 (0.5 g) in THF (2.0 g). The mixture was stirred overnight at room temperature and then the mixture was poured into deionized water within a beaker. The solid was filtered and was dried overnight in a vacuum oven at room temperature and 66.7 Pa (0.5 mm Hg) to afford 0.65 g of product.

Example 7

Preparation of

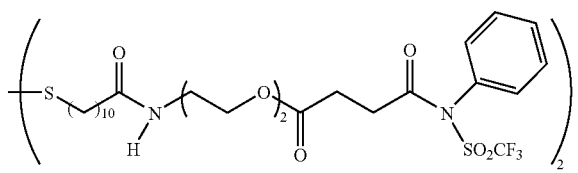

A solution of N-phenyltrifluoromethanesulfonamide (0.28 g) and N,N-diisopropylethylamine (0.16 g) in THF (1.2 g) was slowly added to a stirred solution of the chlorocarbonyl containing product of Preparative Example 6 (0.5 g) in THF (2.0 g). The mixture was stirred overnight at room temperature and then the mixture was poured into deionized water within a beaker. The solid was filtered and was dried overnight in a vacuum oven at room temperature and 66.7 Pa (0.5 mm Hg) to afford 0.72 g of product.

Example 8

Preparation of

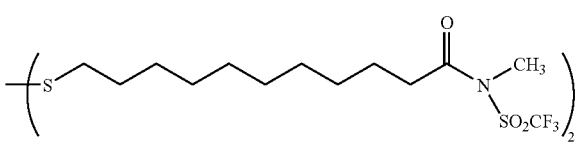

A solution of N-methyltrifluoromethanesulfonamide (0.353 g) and N,N-diisopropylethylamine (0.274 g) in dry THF (1.1 g) was added to a stirred solution of the product of Preparative Example 3 (1.0 g) in dry THF (4.0 g) in a round bottom flask. The mixture was magnetically stirred at room temperature overnight. The mixture was then treated with 20 mL of 0.1N aqueous HCl and the mixture was extracted with chloroform. The organic phase was washed with saturated aqueous NaCl and was dried over anhydrous $MgSO_4$. The volatile materials were removed using a rotary evaporator. Analysis of the residue by $^1H$ NMR spectroscopy indicated that the reaction was not complete. The product residue was transferred to a round bottom flask and was combined with thionyl chloride (0.3 g) and methylene chloride (5 mL). This mixture was magnetically stirred overnight and then the volatile components were removed using a rotary evaporator. A solution of N-methyltrifluoromethanesulfonamide (0.353 g) and N,N-diisopropylethylamine (0.274 g) in dry THF (1.1 g) was then added to the flask and the mixture was magnetically stirred overnight at room temperature. The mixture was then treated with 20 mL of 0.1N aqueous HCl and the mixture was extracted with chloroform. The organic phase was washed with saturated aqueous NaCl and was dried over anhydrous $MgSO_4$. The volatile materials were removed using a rotary evaporator, and then a high vacuum pump, to afford 0.55 g of product.

Example 9

Preparation of

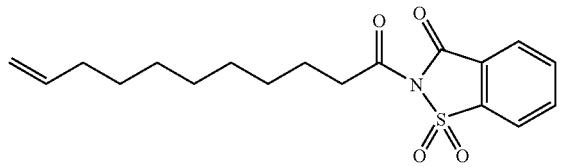

A mixture of 2,3-dihydro-3-oxobenzisosulfonazole (5.0 g), triethylamine (3.3 g) and acetonitrile (30 g) in a round bottom flask was magnetically stirred under a nitrogen atmosphere and was cooled in an ice bath. A solution of 10-undecenoyl chloride (6.1 g) in THF (12 g) was slowly added to the flask using a pressure-equalizing addition funnel. The mixture was allowed to warm to room temperature and was then filtered. The filtrate was concentrated to dryness using a rotary evaporator and the residue was triturated with diethyl ether. The resultant solid was filtered, washed with diethyl ether, and dried in air at room temperature to afford 8.7 g of product.

Example 10

Preparation of

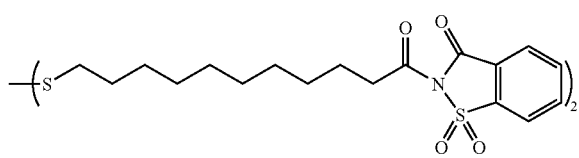

A solution of saccharin (1.8 g) and pyridine (0.8 g) in acetonitrile (8.0 g) was added to a stirred solution of the chlorocarbonyl-containing product of Preparative Example 3 (2.2 g) in acetonitrile (7.8 g). After mixing overnight, most of the solvent was removed using a rotary evaporator and the remainder of the mixture was poured into deionized water in a beaker. The resultant solid was filtered, washed sequentially with isopropyl alcohol and diethyl ether, and was dried overnight in a vacuum oven at room temperature and 66.7 Pa (0.5 mm Hg) to afford 3.5 g of product.

Example 11

Preparation of

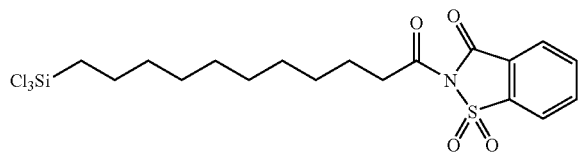

A mixture of the ethylenically unsaturated containing product of Example 9 (4.0 g), trichlorosilane (3.1 g), and methylene chloride (25 g) was combined in a 125 mL screw cap bottle. Platinum(0)-1,3-divinyl-1,1,3,3-tetramethyldisilane complex in xylenes was diluted with methylene chloride to a concentration of approximately 1.5 weight percent, and 3 drops of this solution were added to the bottle. The bottle was then sealed and was heated to 60° C. in a water bath. After 18 hours, the mixture was allowed to cool to room temperature and additional platinum complex solution (1 drop) was added. The bottle was again sealed and was heated at 60° C. for an additional 24 hours. The mixture was then cooled to room temperature and the volatile components were removed using a rotary evaporator.

Example 12

Attachment of a N-sulfonylaminocarbonyl Containing Tethering Group to a Gold-Coated Silicon Substrate A 250-micromolar solution of the disulfide containing product of Example 10 in acetone was prepared. A 1 cm by 1 cm portion of a gold-coated silicon wafer was immersed in the solution for 30 minutes, after which time it was removed and was rinsed sequentially with ethanol and methanol and was then dried by directing a stream of nitrogen gas over the treated gold surface for approximately 1 minute. The ellipsometric thickness on the gold side of the multilayer substrate was determined to be 18 Angstroms. The static advancing contact angle of deionized water on the surface resulting from the attachment of the tethering groups to the gold substrate layer was determined to be 62 degrees.

Example 13

Attachment of a N-sulfonylaminocarbonyl Containing Tethering Group to Multilayer Substrate Of Glass-DLC-DLG A 1-millimolar solution of the trichlorosilyl containing product of Example 11 in methylene chloride was prepared. A multilayer substrate of glass-DLC-DLG, the product of Preparative Example 9, was immersed in this solution for 30 minutes, after which time it was rinsed with methylene chloride and was dried by directing a stream of nitrogen gas over the treated gold surface for approximately 1 minute. The static advancing contact angle of deionized water on the surface resulting from the attachment of tethering groups to the DLG substrate layer was determined to be 63 degrees.

Example 14

Attachment of a N-sulfonylaminocarbonyl Containing Tethering Group to a Multilayer DLG-DLC-polyimide-DLC-DLG Substrate A 1 millimolar solution of the trichlorosilyl product of Example 11 in methylene chloride was prepared. A sample a DLG-DLC-polyimide-DLC-DLG multilayer substrate, approximately 2.5 cm by 7 cm, the product of Preparative Example 8, was immersed in this solution for 30 minutes, after which time both sides were rinsed with methylene chloride and the sample was dried by directing a stream of nitrogen gas over both DLG surfaces for approximately 1 minute each. The static advancing contact angle of deionized water on a surface resulting from attachment of the tethering groups to the DLG substrate layer was determined to be 63 degrees.

Example 15

Attachment of a N-sulfonylaminocarbonyl Containing Tethering Group to a Multilayer Polyimide-Titanium-Gold Substrate A 1 millimolar solution of the disulfide product of Example 10 in acetone was prepared. A sample a polyimide-titanium-gold multilayer substrate, approximately 2.5 cm by 7 cm, the product of Preparative Example 10, was immersed in this solution for 30 minutes, after which time both sides were rinsed with acetone and the sample was dried by directing a stream of nitrogen gas over the gold surface for approximately 1 minute each. The static advancing contact angle of deionized water on the surface resulting from attachment of the tethering groups to the gold substrate layer was determined to be 63 degrees.

Examples 16-17

Immobilization of Lysine with N-sulfonylaminocarbonyl Containing Group Attached to a Gold Coated Silicon Substrate Two 1 cm by 1 cm samples of the product of Example 12 (a N-sulfonylaminocarbonyl containing tethering group attached to a gold-coated silicon substrate) were immersed in a 1 millimolar solution of lysine in carbonate buffer. One of the samples (Example 16) was removed from the buffer after 30 minutes and was rinsed with deionized water. The ellipsometric thickness was determined as described above. The second sample (Example 17) was removed from the buffer after 90 minutes and was rinsed with deionized water before the ellipsometric thickness was determined. The data are given in Table 1 for the thickness of the layer attached to the gold substrate surface.

Comparative Example 1-2

Immobilization of Lysine with N-acyloxysuccinimide-Containing Tethering Group Attached to a Gold-Coated Silicon Substrate Two 1 cm by 1 cm samples of the product of Preparative Example 11 (N-acyloxysuccinimide containing tethering group attached to a gold-coated silicon substrate) were immersed in a 1 millimolar solution of lysine in carbonate buffer. One of the samples was removed from the buffer after 30 minutes (Comparative Example 1) and was rinsed with deionized water. The ellipsometric thickness was determined as described above. The second sample (Comparative Example 2) was removed from the buffer after 90 minutes and was rinsed with deionized water before the ellipsometric thickness was determined. The data are given in Table 1 for the thickness of the layer attached to the gold substrate surface.

TABLE 1

Examples 16-17 and Comparative Examples 1-2

| Example | Time in Lysine Solution | Change in Ellipsometric Thickness (Angstroms) |
| --- | --- | --- |
| 16 | 30 | 3 |
| Comparative Example 1 | 30 | 2 |
| 17 | 90 | 6 |
| Comparative Example 2 | 90 | 4 |

Example 18

Immobilization of Fluorescent Labeled IgG with a N-sulfonylaminocarbonyl Containing Tethering Group Attached to a Multilayer Substrate of Glass-DLC-DLG Fluorescent labeled mouse IgG was reconstituted by mixing 0.55 mL of deionized water to give a solution of the IgG with a concentration of 2 mg/mL. This solution was diluted with CHES buffer to a IgG concentration of 50 μg/mL. Successive dilutions were made to give samples with IgG concentrations of 50 μg/mL, 25 μg/mL, 12.5 μg/mL, and 6.25 μg/mL. An aliquot (15 μL) of each of the IgG solutions was deposited via pipet onto a different portion of the product of Example 13 (a N-sulfonylaminocarbonyl containing tethering group attached to a multilayer substrate of Glass-DLC-DLG). The aliquots were smeared across the surface of the slide using the tip of the pipet. The IgG solution was allowed to stand on the glass slide for 30 minutes, then the slide was washed with sequentially with PBS buffer, PBS buffer containing 0.05 weight percent TWEEN 20, and PBS buffer. The slide was then allowed to dry in air at room temperature for approximately 1 hour. The slide was analyzed using a Model GeneTAC UC-4 scanner (available from Genomic Solutions, Inc., Ann Arbor, Mich.). The results, shown in FIG. 1, indicate that the fluorescent labeled mouse IgG is bound to the surface of the substrate. Qualitative fluorescence intensity is highest with the most concentrated fluorescent labeled IgG sample and lowest with the least concentrated IgG sample.

Example 19

Capture of *Staphylococcus aureus* with Immobilized IgG on Multilayer Substrate of DLG-DLC-polyimide-DLC-DLG Rabbit IgG specific to *Staphylococcus aureus* (rabbit anti *Staphylococcus aureus*, obtained from Accurate Chemical & Scientific Corp., Westbury, N.Y.) was used at a concentration of 4.52 mg/mL. This solution was diluted with CHES buffer to give a solution with a concentration of the IgG of 50 μg/mL. A 1 cm by 1 cm sample of the product of Example 14 (N-sulfonylaminocarbonyl containing tethering group attached to a multilayer substrate of DLG-DLC-polyimide-DLC-DLG; that is, the substrate was polyimide coated on both sides with a layer of DLC and then a layer of DLG) was immersed in this solution for 30 minutes after which time it was washed sequentially with PBS buffer, PBS buffer containing 0.05 weight percent TWEEN 20, and PBS buffer. The sample with immobilized IgG was then allowed to dry in air at room temperature for approximately 1 hour.

A solution of acridine orange in deionized water at a concentration of 10 mg/mL (obtained from Molecular Probes, Inc., Eugene, Oreg.) was diluted to a concentration of 0.1 mg/mL with deionized water. A 500 microliter aliquot of this solution was mixed in a centrifuge tube with a 500 microliter aliquot of a suspension of *Staphylococcus aureus* in PBS buffer at a concentration of 109 colony forming units per milliliter (cfu/mL). This mixture was allowed to stand at room temperature for 15 minutes, after which time it was mixed using a laboratory vortex mixer and was then centrifuged at 8000 rpm. The supernatant liquid was removed using a pipette and the bacteria were washed three times by adding 500 microliters of deionized water to the tube, mixing the contents using the vortex mixer, centrifuging the tube at 8000 rpm, and removing the supernatant liquid. The bacteria were then dispersed in PBS buffer by adding 500 microliters of buffer to the centrifuge tube and mixing the contents by using the vortex mixer. The concentration of *S. aureus* in the buffer was $10^9$ colony forming units per milliliter ($10^9$ cfu/mL).

Figure 2:
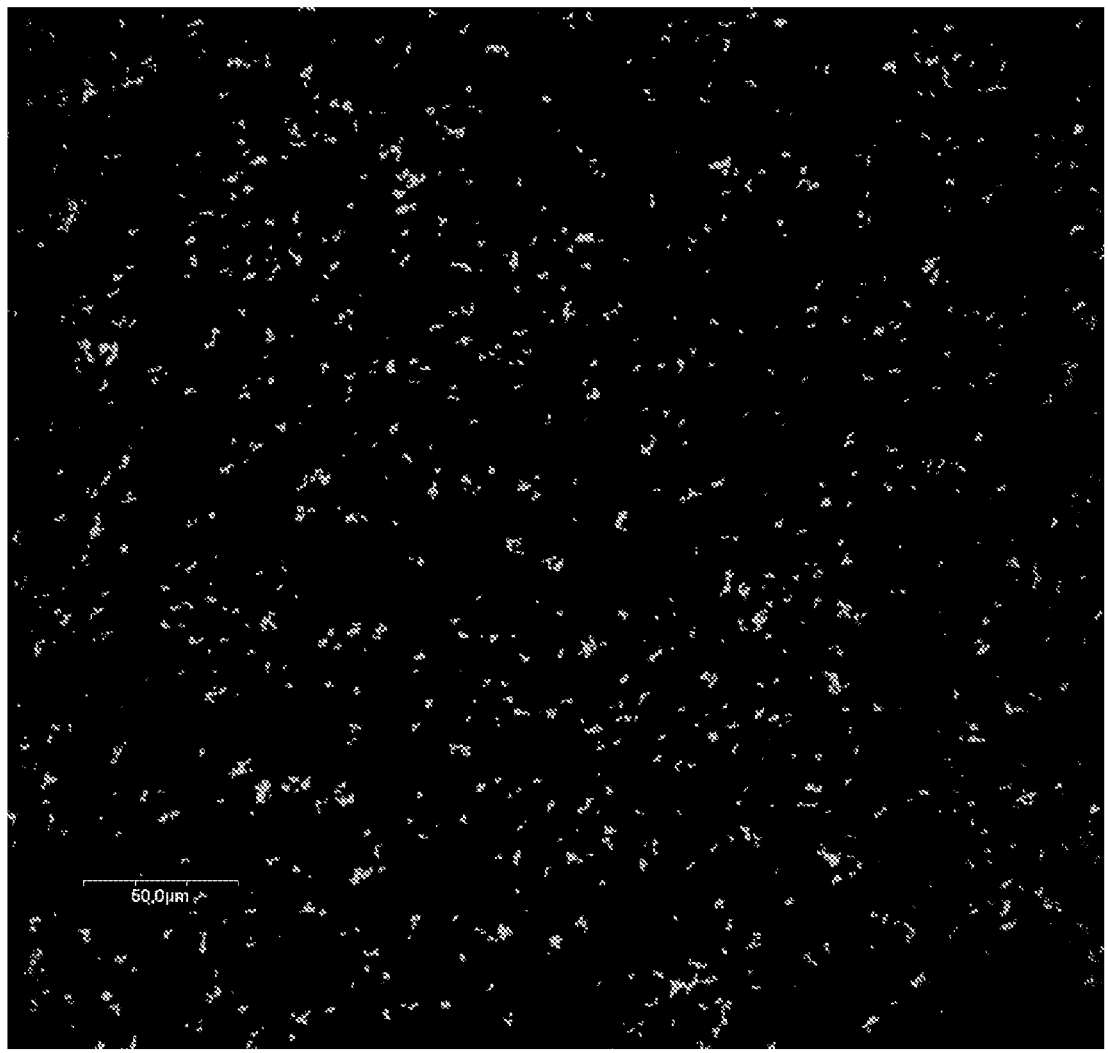
FIG. 2 is a confocal micrograph showing the capture of *Staphylococcus aureus* with IgG immobilized on a multilayer substrate of diamond-like glass/diamond-like carbon/polyimide/diamond-like carbon/diamond-like glass.

The substrate with immobilized IgG was then affixed to a glass microscope slide using double-sided adhesive tape (available from 3M Company, St. Paul, Minn.) and this construction was immersed in the suspension of *S. aureus* in PBS buffer for 1 hour. The sample was then washed sequentially with PBS buffer, PBS buffer containing 0.05 weight percent TWEEN 20, and PBS buffer. The sample was then immersed in a 1 weight percent aqueous solution of paraformaldehyde for 15 minutes, after which time it was washed with deionized water. The sample was analyzed by confocal microscopy using an Olympus Model FV-300 confocal microscope (available from Leeds Precision Inc., Minneapolis, Minn.). The results are shown in FIG. 2.

Comparative Example 3

Figure 3:
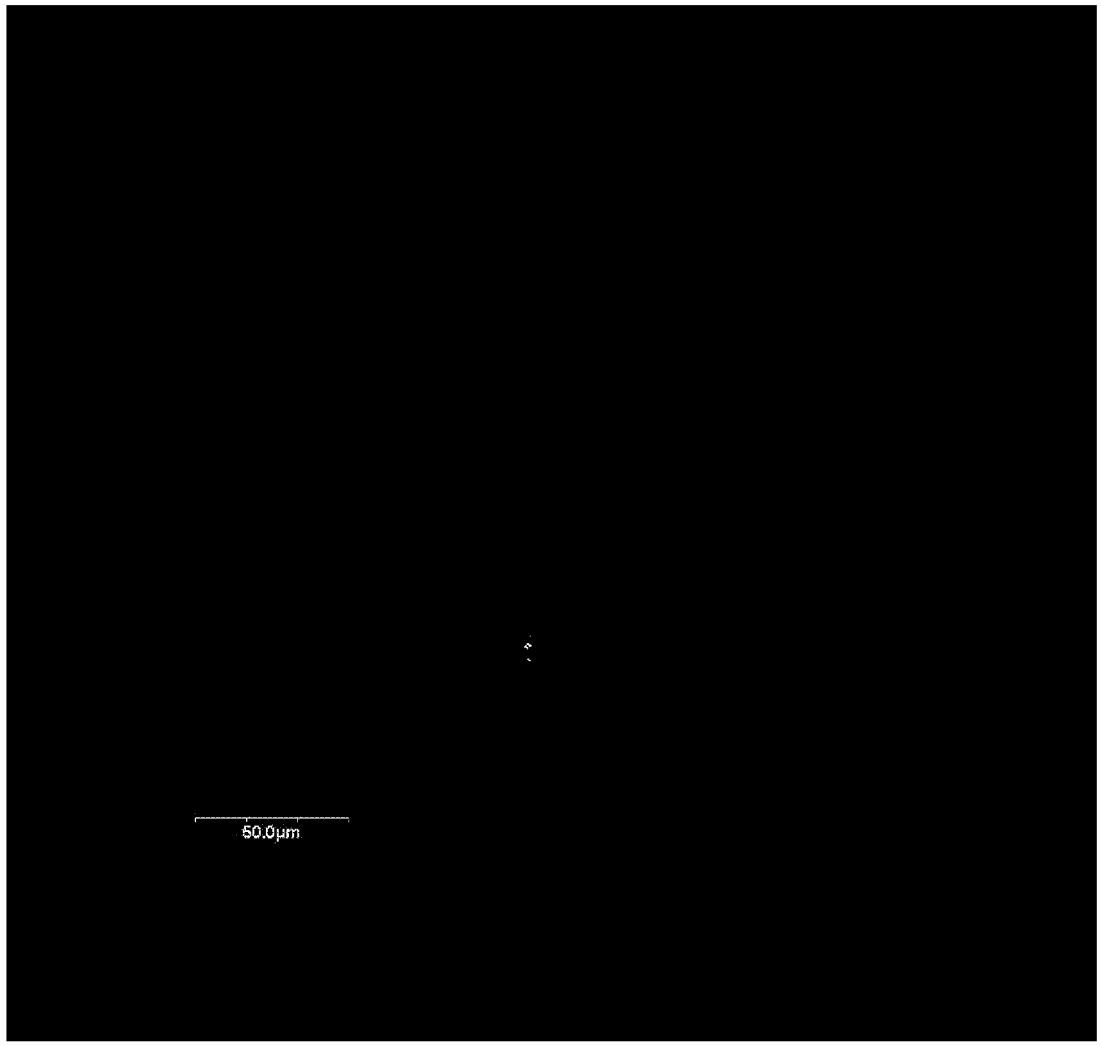
FIG. 3 is a confocal micrograph showing the exposure of *Staphylococcus aureus* with a multilayer substrate of diamond-like glass/diamond-like carbon/polyimide/diamond-like carbon/diamond like glass without IgG immobilized to the substrate with a connector group derived from a compound of Formula I.

Exposure of *Staphylococcus aureus* to Multilayer Substrate of DLG-DLC-polyimide-DLC-DLG A 1 cm by 1 cm sample of the substrate of Preparative Example 8 (multilayer substrate of DLG-DLC polyimide film-DLC-DLG) was immersed CHES buffer for 30 minutes after which time it was washed sequentially with PBS buffer, PBS buffer containing 0.05 weight percent TWEEN 20, and PBS buffer. The substrate was then allowed to dry in air at room temperature for approximately 1 hour. The substrate was then immersed in a suspension of *Staphylococcus aureus* and was then rinsed and immersed in a 1 weight percent aqueous paraformaldehyde solution as described in Example 19. The sample was analyzed by confocal microscopy using an Olympus Model FV-300 confocal microscope (available from Leeds Precision Inc., Minneapolis, Minn.). The results are shown in FIG. 3.

Examples 20-35

ELISA using a Multilayer Substrate of DLG-DLC-polyimide-DLC-DLG having Attached N-Sulfonylaminocarbonyl Containing Tethering Groups For each of Examples 20-35, a 1 cm by 1 cm sample of the product of Example 14 (a multilayer substrate of DLG-DLC-polyimide-DLC-DLG with attached N-sulfonylaminocarbonyl containing tethering groups) was placed in a sterile culture tube that contained CHES buffer (1 mL) and various concentrations of the antibody anti-human mouse IgG. Four tubes each contained a concentration of anti-human mouse IgG in CHES buffer of 5 μg/mL, 10 μg/mL, 20 μg/mL, or 50 μg/mL. Each tube was shaken on a laboratory shaker for an exposure time of 5, 10, 30, or 60 minutes. The buffer was removed from each tube using a pipette and then the substrate immobilized IgG sample in each tube was washed three times with PBS buffer that contained 0.05 weight percent TWEEN 20.

To each tube there was then added 1.5 mL of a solution of 2 weight percent nonfat dry milk powder (available under the trade designation "NESTLE CARNATION NONFAT DRY MILK POWDER" from Nestle USA, Glendale, Calif.) in PBS buffer. Each tube was placed on the shaker for 1 hour after which time the solution was removed using a pipette and then the sample in each tube was washed three times with PBS buffer that contained 0.05 weight percent TWEEN 20.

A 1 mL aliquot of a solution of biotin-conjugated human IgG in PBS buffer, at a concentration of 4 μg/mL, was then added to each tube. The tubes were placed on the shaker for 1 hour after which time the solution was removed using a pipette and then the sample in each tube was washed three times with PBS buffer that contained 0.05 weight percent TWEEN 20. A 1 mL aliquot of a solution of the detecting enzyme SA-HRP in PBS buffer, at a concentration of 0.5 μg/mL, was added to the tubes. The tubes were placed on the shaker for 30 minutes, after which time the solution was removed from each tube using a pipette. Then the sample film in each tube was washed three times with PBS buffer that contained 0.05 weight percent TWEEN 20.

A 1 mL aliquot of the ABTS indicator solution was added to each tube and, after 5 minutes, a solution of 1 weight percent aqueous SDS solution (1 mL) was added. An aliquot of the solution in each tube was transferred to a standard cuvette and the absorbance of each solution at 405 nm was measured using a Model 8453 ultraviolet/visible spectrophotometer (available from Hewlett-Packard Co., Palo Alto, Calif.) The data are given in Table 2.

TABLE 2

ELISA Examples 20-35

| Example | Antibody Concentration (μg/mL) | Exposure Time (min) | Absorbance at 405 nm (relative units) |
|---|---|---|---|
| 20 | 5 | 5 | 0.0651 |
| 21 | 5 | 10 | 0.2467 |
| 22 | 5 | 30 | 0.3441 |
| 23 | 5 | 60 | 0.4367 |
| 24 | 10 | 5 | 0.2466 |
| 25 | 10 | 10 | 0.4157 |
| 26 | 10 | 30 | 0.4146 |
| 27 | 10 | 60 | 0.4418 |
| 28 | 20 | 5 | 0.4442 |
| 29 | 20 | 10 | 0.4147 |
| 30 | 20 | 30 | 0.4694 |
| 31 | 20 | 60 | 0.5261 |
| 32 | 50 | 5 | 0.5358 |
| 33 | 50 | 10 | 0.4418 |
| 34 | 50 | 30 | 0.5082 |
| 35 | 50 | 60 | 0.5262 |

Examples 36-41

Immobilization of Lysine to a N-Sulfonylaminocarbonyl Containing Compound Attached to a Multilayer Substrate of Glass-DLC-DLG Six samples of the product of Example 13 (a N-sulfonylaminocarbonyl containing tethering group to attached to a multilayer substrate of Glass-DLC-DLG) having a static advancing contact angle of deionized water of 63 degrees, were immersed in a 30 millimolar solution of lysine in CHES buffer. A sample was removed at time intervals, as shown in Table 3, and was washed with CHES buffer and dried under stream of nitrogen gas. The contact angle was then measured for the layer attached to the DLG surface of the multilayer substrate as described above. The data are shown in Table 3.

TABLE 3

Examples 36-41

| Example | Time (min) | Contact Angle |
|---|---|---|
| 36 | 1 | 23° |
| 37 | 2 | 23° |
| 38 | 5 | 23° |
| 39 | 10 | 23° |
| 40 | 30 | 23° |
| 41 | 60 | 23° |

Examples 42-46

Immobilization of HSA to a Gold-Coated Silicon Substrate with N-sulfonylaminocarbonyl Containing Tethering Groups Five samples of the product of Example 12 (N-sulfonylaminocarbonyl containing tethering group attached to a gold-coated silicon substrate) were immersed in a 10 micromolar solution of HSA in carbonate buffer at pH 9.6. A sample was removed at time intervals, as shown in Table 4, and was washed sequentially with deionized water, ethanol, and methanol and was then measured dried under a stream of nitrogen gas. The ellipsometric thickness was then measured as described above and was compared to the thickness of the product of Example 12 (18 Angstroms). That is, the thickness of the layer attached to the gold surface of the substrate was measured. The data are shown in Table 4.

TABLE 4

Examples 42-46

| Example | Time (min) | Increase in Ellipsometric Thickness (Angstroms) |
|---|---|---|
| 42 | 0.1 | 12 |
| 43 | 15 | 12 |
| 44 | 30 | 11 |
| 45 | 60 | 12 |
| 46 | 90 | 15 |

Comparative Examples 4-7

Binding of HSA to a N-acyloxysuccinimide-Containing Tethering Attached to a Gold-Coated Silicon Substrate Four samples of the product of Preparative Example 11 (N-acyloxysuccinimide containing tethering groups attached to a gold-coated silicon substrate) were immersed in a 10 micromolar solution of HSA in carbonate buffer at pH 9.6. A sample was removed at time intervals, as shown in Table 5, and was washed sequentially with deionized water, ethanol and methanol and was then dried under a stream of nitrogen gas. The ellipsometric thickness was then measured as described above and was compared to the thickness of the film as prepared as described in Preparative Example 11 (17 Angstroms). That is, the thickness of the layer attached to the gold surface of the substrate was measured. The data are shown in Table 5.

TABLE 5

Comparative Examples 4-7

| Comparative Example | Time (min) | Increase in Ellipsometric Thickness (Angstroms) |
|---|---|---|
| 4 | 0.1 | 2 |
| 5 | 15 | 5 |
| 6 | 60 | 5 |
| 7 | 90 | 10 |

Example 47

Attachment of a N-methyl-trifluoromethanesulfonamide Containing Tethering Group to a Gold-Coated Silicon Substrate A 250-micromolar solution of the disulfide containing product of Example 8 in methyl ethyl ketone was prepared. A 1 cm by 1 cm portion of a gold-coated silicon wafer was immersed in the solution for 30 minutes, after which time it was removed and was rinsed sequentially with ethanol and methanol and was then dried by directing a stream of nitrogen gas over the treated gold surface for approximately 1 minute. The ellipsometric thickness was determined to be 17 Angstroms and the static advancing contact angle of deionized water on the surface resulting from the attachment of the tethering groups to the gold substrate layer was determined to be 79 degrees.

Example 48

Attachment of a N-phenyl-trifluoromethanesulfonamide Containing Tethering Group to a Gold-Coated Silicon Substrate A 250-micromolar solution of the disulfide containing product of Example 4 in methyl ethyl ketone was prepared. A 1 cm by 1 cm portion of a gold-coated silicon wafer was immersed in the solution for 30 minutes, after which time it was removed and was rinsed sequentially with ethanol and methanol and was then dried by directing a stream of nitrogen gas over the treated gold surface for approximately 1 minute. The ellipsometric thickness was determined to be 23 Angstroms and the static advancing contact angle of deionized water on the surface resulting from the attachment of the tethering groups to the gold substrate layer was determined to be 73 degrees.

Example 49

Immobilization of 1-aminododecane with N-methyltrifluoromethanesulfonamine-Containing Group Attached to a Gold Coated Silicon Substrate A 1 cm by 1 cm sample of the product of Example 47 (a N-methyltrifluoromethanesulfonamide containing tethering group attached to a gold-coated silicon substrate) was immersed in a 1 millimolar solution of 1-aminododecane in ethanol. The sample was removed from the solution after 2 hours and was rinsed sequentially with ethanol and methanol and was then dried under a stream of nitrogen gas. The ellipsometric thickness was determined to be 21 Angstroms and the static advancing contact angle of deionized water on the surface was determined to be 86 degrees.

Example 50

Immobilization of didodecylamine with N-methyltrifluoromethanesulfonamine-Containing Group Attached to a Gold Coated Silicon Substrate A 1 cm by 1 cm sample of the product of Example 47 (a N-methyltrifluromethanesulfonamide containing tethering group attached to a gold-coated silicon substrate) was immersed in a 1 millimolar solution of didodecylamine in ethanol. The sample was removed from the solution after 2 hours and was rinsed sequentially with ethanol and methanol and was then dried under a stream of nitrogen gas. The ellipsometric thickness was determined to be 19 Angstroms and the static advancing contact angle of deionized water on the surface was determined to be 78 degrees.

Example 51

Immobilization of 1-aminododecane with N-phenyltrifluoromethanesulfonamine-Containing Group Attached to a Gold Coated Silicon Substrate A 1 cm by 1 cm sample of the product of Example 48 (a N-phenyltrifluromethanesulfonamide containing tethering group attached to a gold-coated silicon substrate) was immersed in a 1 millimolar solution of 1-aminododecane in ethanol. The sample was removed from the solution after 2 hours and was rinsed sequentially with ethanol and methanol and was then dried under a stream of nitrogen gas. The ellipsometric thickness was determined to be 26 Angstroms and the static advancing contact angle of deionized water on the surface was determined to be 78 degrees.

Example 52

Immobilization of Didodecylamine with N-phenyltrifluoromethanesulfonamine-Containing Group Attached to a Gold Coated Silicon Substrate A 1 cm by 1 cm sample of the product of Example 48 (a N-phenyltrifluromethanesulfonamide containing tethering group attached to a gold-coated silicon substrate) was immersed in a 1 millimolar solution of didodecylamine in ethanol. The sample was removed from the solution after 2 hours and was rinsed sequentially with ethanol and methanol and was then dried under a stream of nitrogen gas. The ellipsometric thickness was determined to be 23 Angstroms and the static advancing contact angle of deionized water on the surface was determined to be 78 degrees.

Example 53

Capture of Staphylococcus aureus With immobilized IgG on Multilayer Substrate of Polyimide-Titanium-Gold Rabbit IgG specific to Staphylococcus aureus (rabbit anti Staphylococcus aureus, obtained from Accurate Chemical & Scientific Corp., Westbury, N.Y.) was used at a concentration of 4.52 mg/mL. This solution was diluted with CHES buffer to give a solution with a concentration of the IgG of 50 µg/mL. A 1 cm by 1 cm sample of the product of Example 15 (N-sulfonylaminocarbonyl containing tethering group attached to a multilayer substrate of polyimide-titanium-gold as described in Preparative Example 10) was immersed in this solution for 30 minutes after which time it was washed sequentially with PBS buffer, PBS buffer containing 0.05 weight percent TWEEN 20, and PBS buffer. The sample with immobilized IgG was then allowed to dry in air at room temperature for approximately 1 hour.

A solution of acridine orange in deionized water at a concentration of 10 mg/mL (obtained from Molecular Probes, Inc., Eugene, Oreg.) was diluted to a concentration of 0.1 mg/mL with deionized water. A 500 microliter aliquot of this solution was mixed in a centrifuge tube with a 500 microliter aliquot of a suspension of Staphylococcus aureus in deionized water at a concentration of $10^9$ colony forming units per milliliter (cfu/mL). This mixture was allowed to stand at room temperature for 15 minutes, after which time it was mixed using a laboratory vortex mixer and was then centrifuged at 8000 rpm. The supernatant liquid was removed using a pipette and the bacteria were washed three times by adding 500 microliters of deionized water to the tube, mixing the contents using the vortex mixer, centrifuging the tube at 8000 rpm, and removing the supernatant liquid. The bacteria were then dispersed in PBS buffer by adding 500 microliters of buffer to the centrifuge tube and mixing the contents by using the vortex mixer. The concentration of S. aureus in the buffer was 109 colony forming units per milliliter ($10^9$ cfu/mL).

Figure 4:
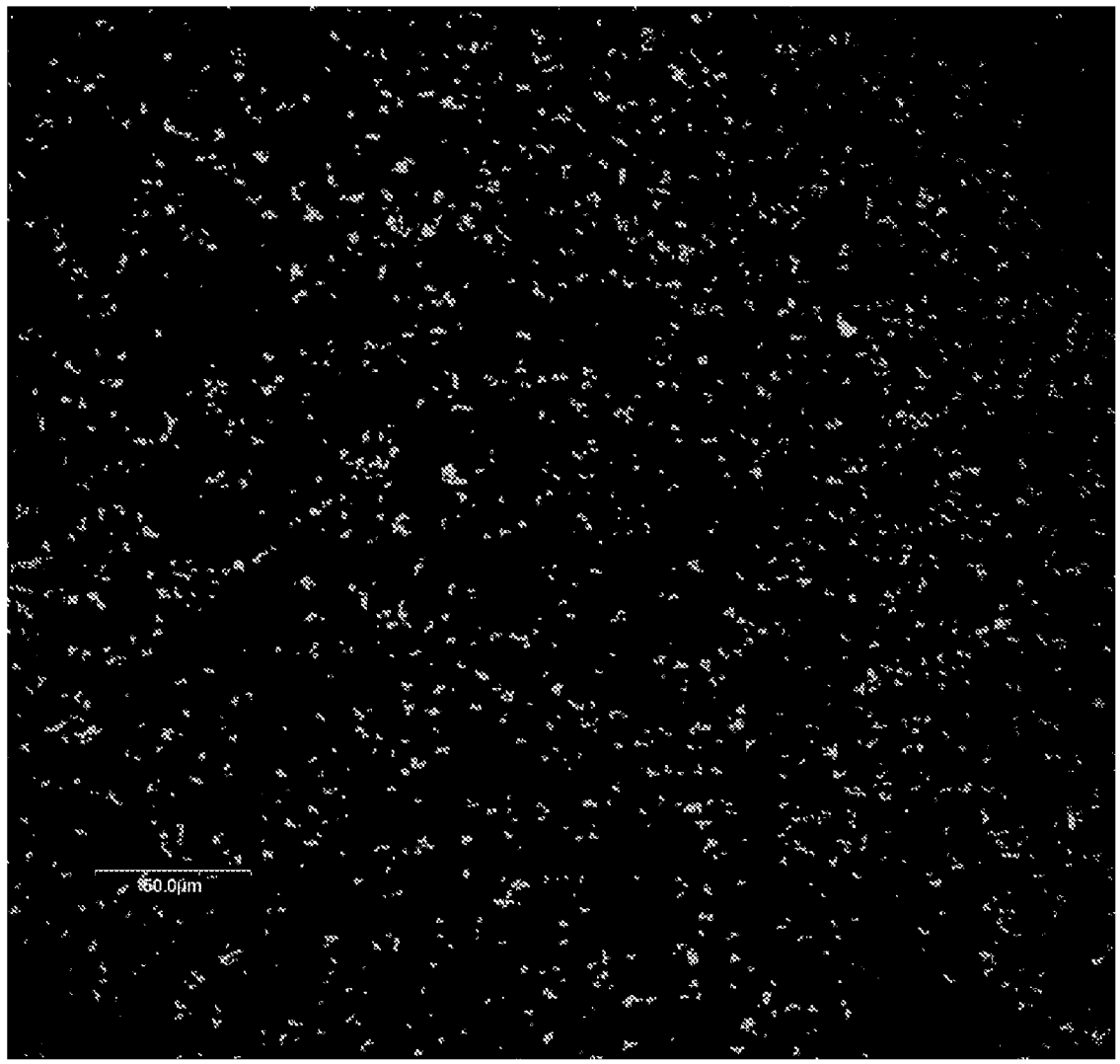
FIG. 4 is a confocal micrograph showing capture of *Staphylococcus aureus* with IgG immobilized on a multilayer substrate of polyimide/titanium/gold.

The substrate with immobilized IgG was then affixed to a glass microscope slide using double-sided adhesive tape (available from 3M Company, St. Paul, Minn.) and this construction was immersed in the suspension of S. aureus in PBS buffer for 1 hour. The sample was then washed sequentially with PBS buffer, PBS buffer containing 0.05 weight percent TWEEN 20, and PBS buffer. The sample was then immersed in a 1 weight percent aqueous solution of paraformaldehyde for 15 minutes, after which time it was washed with deionized water. The sample was analyzed by confocal microscopy using an Olympus Model FV-300 confocal microscope (available from Leeds Precision Inc., Minneapolis, Minn.). The results are shown in FIG. 4.

Comparative Example 8

Figure 5:
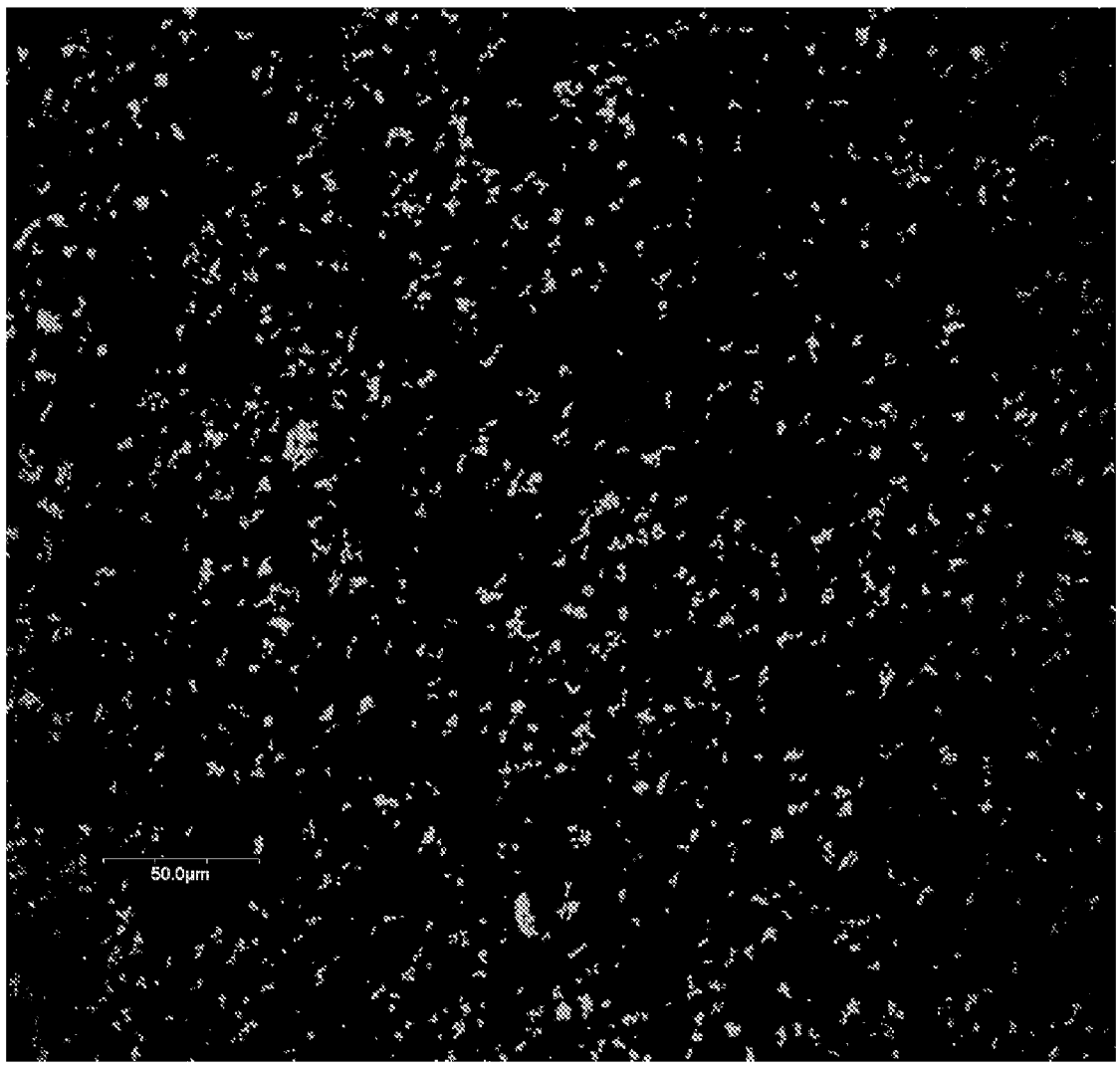
FIG. 5 is a confocal micrograph showing the exposure of *Staphylococcus aureus* to a multilayer substrate of polyimide/titanium/gold without IgG immobilized to the substrate.

Exposure of Staphylococcus aureus to Multilayer Substrate of Polyimide-Titanium-Gold A 1 cm by 1 cm sample of the substrate of Preparative Example 10 (multilayer substrate of polyimide film-titanium-gold) was immersed CHES buffer for 30 minutes after which time it was washed sequentially with PBS buffer, PBS buffer containing 0.05 weight percent TWEEN 20, and PBS buffer. The substrate was then allowed to dry in air at room temperature for approximately 1 hour. The substrate was then immersed in a suspension of S. aureus and was then rinsed and immersed in a 1 weight percent aqueous paraformaldehyde solution as described in Example 53. The sample was analyzed by confocal microscopy using an Olympus Model FV-300 confocal microscope (available from Leeds Precision Inc., Minneapolis, Minn.). The results are shown in FIG. 5.

Example 54

Attachment of a N-sulfonylaminocarbonyl Containing Tethering Group to a Substrate of poly(methylmethacrylate-co-methacrylic Acid) Beads The hydroxyl functionalized beads of Preparative Example 13 (2.0 g) were combined with NMP (15 mL) in a round bottom flask that was fitted with a magnetic stir bar. The acid chloride product of Example 2 (0.19 g) in NMP (5 mL) was added to the flask. Ethyldiisopropyl amine (0.09 g) in NMP (5 mL) was then added to the flask and the mixture was magnetically stirred at room temperature overnight. The beads were then filtered, washed with isopropyl alcohol and were dried under a stream of nitrogen gas to afford the product as white beads.

Example 55

Immobilization of FITC-Albumin with a N-sulfonylaminocarbonyl Containing Tethering Group Attached to poly(methylmethacrylate-co-methacrylic Acid) Beads The poly(methylmethacrylate-co-methacrylic acid) beads with the N-sulfonylaminocarbonyl containing tethering group of Example 54 (50 mg) was combined with a solution of FITC-albumin (1 mL) in a centrifuge tube. The tube was placed on a laboratory rocker for 45 minutes. The beads were then washed by centrifuging the tube, decanting the supernatant liquid and then adding PBS buffer having a pH of 7.2 (11 mL), again centrifuging the tube and again decanting the supernatant liquid. This washing with PBS buffer was repeated for a total of four washing cycles to afford beads that were yellow-orange in color. The color of the beads thus obtained was compared to the color of the beads of Example 54 that were not treated with FITC-albumin, which were white in color.

What is claimed is:
1. An article comprising:
a substrate;
a substrate-attached tethering group comprising a reaction product of a complementary functional group G on a surface of the substrate with a compound of Formula I

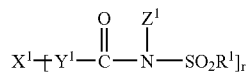

wherein
$X^1$ is a substrate-reactive functional group selected from a carboxy, halocarbonyl, halocarbonyloxy, cyano, hydroxy, mercapto, isocyanato, halosilyl, alkoxysilyl, acyloxysilyl, azido, aziridinyl, haloalkyl, tertiary amino, primary aromatic amino, secondary aromatic amino, disulfide, alkyl disulfide, benzotriazolyl, phosphono, phosphoroamido, or phosphato;

$Y^1$ is a single bond or a divalent group selected from an alkylene, heteroalkylene, arylene, carbonyl, carbonyloxy, carbonylimino, oxy, thio, —$NR^d$—where $R^d$ is hydrogen or alkyl, or combinations thereof;

$Z^1$ is $(CO)R^a$ wherein $R^a$ together with $R^1$ and groups to which they are attached form a four to eight membered heterocyclic or heterobicyclic group having a nitrogen heteroatom and a sulfur heteroatom, wherein said heterocyclic or heterobicyclic group can be fused to an optional aromatic group, optional saturated or unsaturated cyclic group, or optional saturated or unsaturated bicyclic group;

r is equal to 1 when $X^1$ is a monovalent group or equal to 2 when $X^1$ is a divalent group;

G is the complementary functional group capable of reacting with $X^1$ to form an ionic bond, covalent bond, or combinations thereof, wherein the group G is selected from hydroxy, mercapto, primary aromatic amino group, secondary aromatic amino group, secondary aliphatic amino group, azide, carboxyl, carboxylic acid anhydride, isocyanate, halocarbonyl, halocarbonyloxy, acrylate, silanol, or nitrile; and said tethering group is unsubstituted or substituted with a halo, alkyl, alkoxy, or combinations thereof.

2. The article of claim 1, wherein the compound is of formula

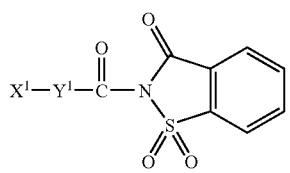

where $X^1$ is monovalent or

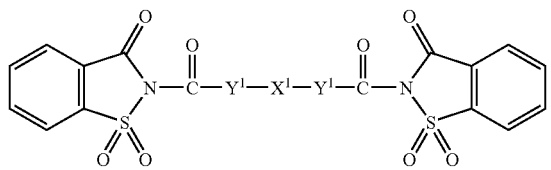

where $X^1$ is divalent.

3. The article of claim 1, wherein the substrate comprises a polymeric material.

4. The article of claim 1, wherein the substrate comprises a polyimide or polyester film.

5. The article of claim 1, wherein the substrate is multilayered and has an outer layer comprising gold.

6. The article of claim 1, wherein the substrate is multilayered and has an outer layer comprising diamond-like glass.

7. The article of claim 1, wherein the substrate is a multilayer substrate comprising;
 a support layer comprising polyimide or polyester;
 an outer layer comprising diamond-like glass;
 and a layer of diamond-like glass positioned between the support layer and the outer layer.

8. The article of claim 1, wherein the substrate is in the form of a bead.

* * * * *

UNITED STATES PATENT AND TRADEMARK OFFICE
CERTIFICATE OF CORRECTION

| | | |
|---|---|---|
| PATENT NO. | : 7,675,058 B2 | |
| APPLICATION NO. | : 11/553822 | |
| DATED | : March 9, 2010 | |
| INVENTOR(S) | : Karl E Benson | |

It is certified that error appears in the above-identified patent and that said Letters Patent is hereby corrected as shown below:

Column 10
Line 59 (Approx.), after "thereof" insert -- . --.

Column 17
Line 48, delete "tetramethysilane" and insert -- tetramethylsilane --, therefor.

Column 20
Line 8, delete "oxycarbonlythio" and insert -- oxycarbonylthio --, therefor.

Column 21
Line 12, after "a" insert -- β- --.

Line 18 (Approx.), after "a" insert -- β- --.

Column 22
Line 3, delete "phosphate" and insert -- phosphato --, therefor.

Column 26
Line 6, delete "thereof," and insert -- thereof; --, therefor.

Column 42
Line 48, after "then" delete "measured".

Column 44
Line 29, delete "N-methyltrifluromethanesulfonamide" and insert -- N-methyltrifluoromethanesulfonamide --, therefor.

Line 46, delete "N-phenyltrifluromethanesulfonamide" and insert -- N-phenyltrifluoromethanesulfonamide --, therefor.

Signed and Sealed this
Twentieth Day of September, 2011

David J. Kappos
*Director of the United States Patent and Trademark Office*

CERTIFICATE OF CORRECTION (continued)
U.S. Pat. No. 7,675,058 B2

Column 44
Line 63, delete "N-phenyltrifluromethanesulfonamide" and insert -- N-phenyltrifluoromethanesulfonamide --, therefor.

Column 47
Line 10 (Approx.), in Claim 1, delete "$Z^1$ is (CO)$R^a$" and insert -- $Z^1$ is -(CO)$R^a$ --, therefor.